United States Patent [19]

Tanaka et al.

[11] Patent Number: 4,960,678
[45] Date of Patent: Oct. 2, 1990

[54] PHOTOCHROMIC COMPOUNDS

[75] Inventors: Takashi Tanaka, Shinnanyo; Satoshi Imura, Tokuyama; Yasuji Kida, Kudamatsu, all of Japan

[73] Assignee: Tokuyama Soda Kabushiki Kaisha, Yamaguchi, Japan

[21] Appl. No.: 403,487

[22] Filed: Sep. 6, 1989

Related U.S. Application Data

[62] Division of Ser. No. 268,497, Nov. 8, 1988, Pat. No. 4,882,438.

[30] Foreign Application Priority Data

Nov. 10, 1987 [JP] Japan ................. 62-282131
Nov. 11, 1987 [JP] Japan ................. 62-283116
Apr. 2, 1988 [JP] Japan ................. 62-80250

[51] Int. Cl.$^5$ ............................. G03C 1/733
[52] U.S. Cl. ..................... 430/332; 430/338; 430/337; 430/343; 430/962; 350/163
[58] Field of Search ............... 430/338, 337, 962, 343, 430/332; 350/163

[56] References Cited

U.S. PATENT DOCUMENTS 4,576,766 3/1986 Baskervill et al. ............... 351/163
4,685,783 8/1987 Heller et al. ............... 351/163

*Primary Examiner*—Paul R. Michl
*Assistant Examiner*—Thorl Chea
*Attorney, Agent, or Firm*—Wenderoth, Lind & Ponack

[57] ABSTRACT

A compound represented by the following general formula [I]

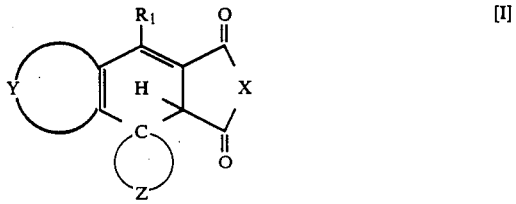

wherein

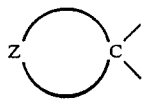

represents a norbornylidene group or an adamantylidene group each of which may have a substituent, and X represents an oxygen atom, the group $>N-R_2$, the group $>N-A_1-B_1+A_2)_{\overline{m}}(B_2)_{\overline{n}}R_3$, the group $>N-A_3-A_4$, or the group $>N-A_3-A_4$, provided that when

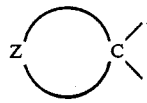

is an adamantylidene group, X is selected from the above groups excepting the oxygen atom and the group $>N-R_2$; and plastic lens containing the compound of the above formula [I].

4 Claims, 2 Drawing Sheets

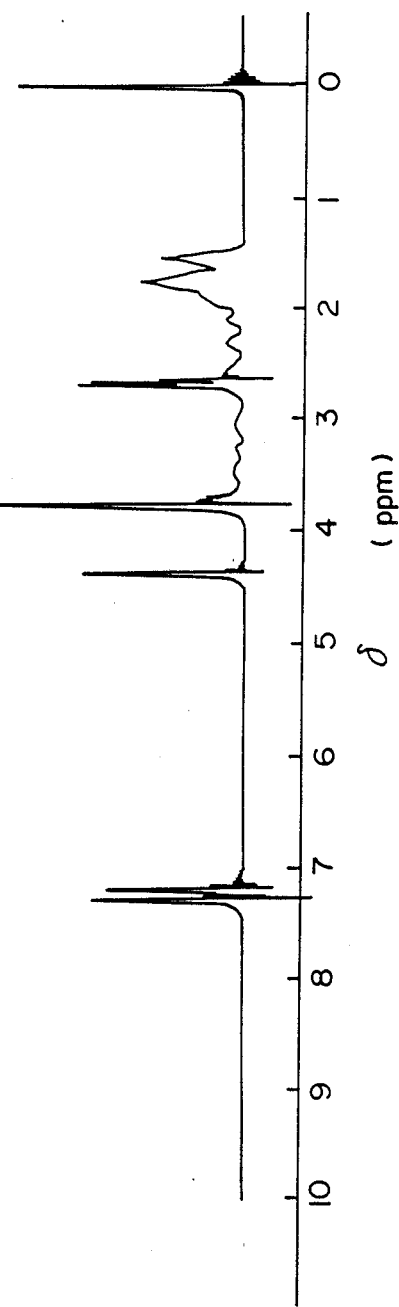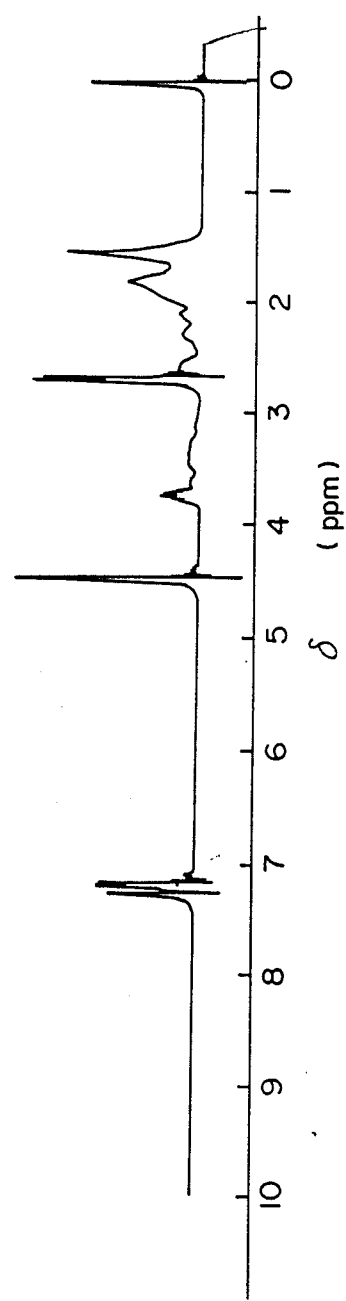

PHOTOCHROMIC COMPOUNDS

This application is a divisional Application of application Ser. No. 268,497 filed Nov. 8, 1988, now U.S. Pat. No. 4,882,438.

This invention relates to a novel compound having a photochromic action, processes for producing it, a composition comprising it, and to its use. More specifically, it relates to a novel compound having excellent durability which changes reversibly in color from a colorless form to a colored form by the action of light containing ultraviolet rays such as sunlight or the light from a mercury lamp, processes for its production, a composition comprising it, and to its use.

Photochromism, which has aroused a particular interest for the last several years, denotes a phenomenon in which when light containing ultraviolet rays such as sunlight or the light from a mercury lamp is irradiated onto a certain compound, its color rapidly changes, and when the light irradiation is stopped and the compound is placed in a dark place, its color reversibly returns to the original color. Compounds having this property are called photochromic compounds. Photochromic compounds of various structures have been synthesized and proposed, but no particular common structure, however, has been observed in these compounds.

Compounds represented by the following general formula

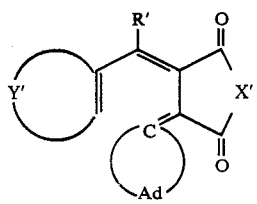

wherein

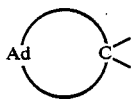

represents a substituted or unsubstituted adamantylidene group, R' represents a hydrogen, an aryl group, an aralkyl group or a heterocyclic group, X' represents oxygen or the group >N—R" in which R" represents a hydrogen atom, an aryl group, an alkyl group or an aralkyl group, and

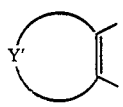

represents an aromatic group or an unsaturated heterocyclic group,
are known as a series of photochromic compounds which absorb ultraviolet rays and are colored and rapidly return to their original color under white light (U.S. Pat. No. 4,220,708). These compounds are not at all colored, or hardly colored, under sunlight because they show a tendency to returning to a coorless form under white light.

Compounds of the above formula are known to be converted by heating into photochromic compounds of the following general formula which are colored under sunlight (see U.K. Patent Application No. 2,146,327)

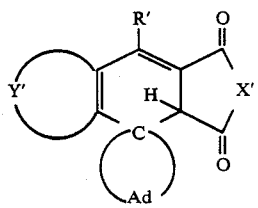

wherein

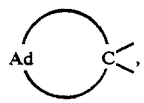

R', X' and

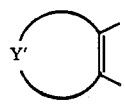

are the same as defined with regard to the above compounds.

It is believed that since the above photochromic compounds have rigid non-flexible cage-like adamantylidene groups, the single bond forming part of the six-membered ring is weakened and an electron cyclic ring-opening by irradiation of solar light is facilitated and consequently, the compounds become colored. The photochromic compounds in the colored state are relatively stable and even when the irradiation of sunlight is stopped, the rate of color fading is not so fast. Furthermore, the photochromic compounds have poor durability upon repetitions of reversible coloration and color erasure.

In the above-cited U. K. Patent Application, X' is defined as oxygen or >N—R", and R" is defined as hydrogen, an aryl group, an alkyl group or an aralkyl group. As preferred examples of R", methyl and phenyl are shown, and only hydrogen is shown as a specific example.

The durability of the above photochromic compound is evaluated by the time $T_{\frac{1}{2}}$ required for the color density to decrease to $\frac{1}{2}$ of its initial value under continuous irradiation from an AM2 lamp in the above U. K. Patent Application. It is described that a compound of the above general formula in which R' is a methyl group, X' is an oxygen atom, and

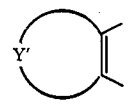

is a thienylene group has a durability of 2,000 minutes. However, when the present inventors determined the durability of the same compound by using a xenon lamp, its $T_{\frac{1}{2}}$ was only 3.5 hours.

Thus, the above photochromic compounds have low durability in the repetition of reversible coloration and color erasure. It has been desired to develop a photochromic compound having sufficient durability.

It is an object of this invention to provide a novel photochromic compound.

Another object of this invention is to provide a compound which reversibly changes from a colorless form to a colored form by the action of ultraviolet rays.

Still another object of this invention is to provide a photochromic compound having durability which can be used for a long period of time.

Yet another object of this invention is to provide a photochromic compound having practical utility.

A further object of this invention is to provide industrially advantageous processes for producing the photochromic compound.

A still further object of this invention is to provide a polymeric composition comprising the photochromic compound.

Other objects of the invention will become apparent from the following description.

These objects and advantages of the invention are achieved by a novel compound represented by the following general formula [I]

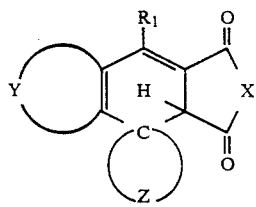

wherein

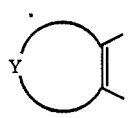

represents a divalent aromatic hydrocarbon group or a divalent unsaturated heterocyclic group each of which may have a substituent, $R_1$ represents a monovalent hydrocarbon group or a monovalent heterocyclic group each of which may have a substituent,

represents a norbornylidene group or an adamantylidene group each of which may have a substituent, and X represents an oxygen atom, the group $>N-R_2$, the group $>N-A_1-B_1(-A_2)_m(-B_2)_n-R_3$, the group $>N-A_3-A_4$, or the group $>N-A_3-R_4$, provided that when

is an adamantylidene group, X is selected from the above groups excepting the oxygen atom and the group $>N-R_2$, in which $R_2$ represents a hydrogen atom, an alkyl group having 1 to 20 carbon atoms, or an aryl group having 6 to 10 carbon atoms, $A_1$ and $A_2$ are identical or different and each represents an alkylene group having 1 to 10 carbon atoms, an alkylidene group having 2 to 10 carbon atoms, a cycloalkylene group having 3 to 10 carbon atoms or an alkylcycloalkanediyl group having 6 to 10 carbon atoms, $B_1$ and $B_2$ are identical or different, and each represents

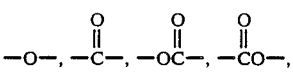

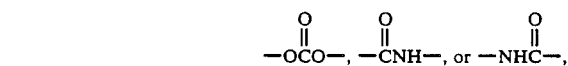

m and n, independently from each other, represent 0 or 1, provided that when m is 0, n is also 0, $R_3$ represents an alkyl group having 1 to 10 carbon atoms, a naphthyl group or a naphthylalkyl group having 1 to 4 carbon atoms in the alkyl moiety, the alkyl group having 1 to 10 carbon atoms being optionally substituted by 1 to 3 atoms or groups selected from the class consisting of halogen atoms, cyano groups and nitro groups, and the naphthyl or naphthylalkyl group being optionally substituted by 1 to 3 atoms or groups selected from the class consisting of halogen atoms, cyano groups, nitro groups, alkylamino groups having 1 to 3 carbon atoms, alkyl groups having 1 to 3 carbon atoms and alkoxy groups having 1 to 3 carbon atoms, $A_3$ represents an alkylene group having 1 to 10 carbon atoms, an alkylidene group having 2 to 10 carbon atoms, a cycloalkylene group having 3 to 10 carbon atoms, or an alkylcycloalkanediyl group having 6 to 10 carbon atoms, $A_4$ represents a naphthyl group which may be substituted by 1 to 3 atoms or groups selected from the class consisting of halogen atoms, cyano groups, nitro groups, alkylamino groups having 1 to 3 carbon atoms, alkyl groups having 1 to 3 carbon atoms and alkoxy groups having 1 to 3 carbon atoms, and $R_4$ represents a halogen atoms, a cyano group or a nitro group.

The compound of the invention represented by general formula [I] will be described below in greater detail.

In general formula [I], the group

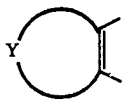

represents an aromatic hydrocarbon group or an unsaturated heterocyclic group, which may have at most five, preferably up to 3, substituents. The aromatic hydrocarbon group has 6 to 20 carbon atoms, preferably 6 to 14 carbon atoms. Examples of the ring forming the aromatic hydrocarbon group are benzene, naphthalene and phenanthrene rings.

The unsaturated heterocyclic group may be a 5- or 6-membered hetero-monocyclic group containing 1 to 3, preferably 1 or 2, hetero atoms selected from nitrogen, oxygen and sulfur atoms, or a condensed heterocyclic group in which a benzene ring or a cyclohexene ring is fused. Examples of the ring forming these heterocyclic groups are nitrogen-containing heterocyclic rings such as a pyrrole ring, a pyridine ring, a quinoline ring, an isoquinoline ring, an imidazole ring and a benzimidazole ring; oxygen-containing heterocyclic rings such as a furan ring, a benzofuran ring and a pyrane ring; sulfur-containing heterocyclic rings such as a thiophene ring and a benzothiophene ring and rings containing two kinds of hetero atoms such as an oxazole ring and a thiazole ring.

As stated above, the aromatic hydrocarbon group or unsaturated heterocyclic group represented by

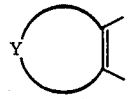

contains at most 5, preferably up to 3, substituents. Examples of the substituents include halogen atoms such as fluorine, chlorine, bromine and iodine; a hydroxyl group; a cyano group; an amino group; a nitro group; a carboxyl group; alkylamino groups having 1 to 4 carbon atoms such as methylamino and diethylamino groups; alkyl groups having 1 to 4 carbon atoms such as methyl, ethyl, propyl and t-butyl groups; halogenated lower alkyl groups containing 1 to 3 halogen atoms such as trifluoromethyl and 2-chloroethyl groups; lower alkoxy groups having 1 to 4 carbon atoms such as methoxy, ethoxy and t-butoxy groups; aryl groups having 6 to 10 carbon atoms such as phenyl, naphthyl and tolyl groups; aryloxy groups containing 6 to 14 carbon atoms such as phenoxy and 1-naphthoxy groups; aralkyl groups having 7 to 15 carbon atoms such as benzyl, phenylethyl and phenylpropyl groups; aralkoxy groups having 7 to 15 carbon atoms such as benzyloxy and phenylpropoxy groups; and alkylthio groups having 1 to 4 carbon atoms. These substituents may be of the same or different kind, and the position of substitution is not particularly limited.

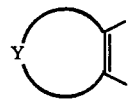

is preferably a divalent aromatic hydrocarbon group or a divalent unsaturated heterocyclic groups, each of which may be substituted by at least one atom or group selected from the class consisting of halogen atoms, a nitro group, a cyano group, an amino group, alkylthio groups having 1 to 4 carbon atoms, aryl groups having 6 to 10 carbon atoms, alkyl groups having 1 to 4 carbon atoms and alkoxy groups having 1 to 4 carbon atoms.

More preferably, it is an aryl group having 6 to 14 carbon atoms, a 5- or 6-membered hetero-monocyclic group containing 1 to 3 hetero atoms selected from nitrogen, oxygen and sulfur atoms, or a condensed heterocyclic group resulting from fusion of a benzene or cyclohexene ring to the heterocyclic group, each of which may be substituted by 1 to 3 substituents described above.

Specifically,

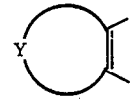

is preferably a benzene ring or a 5- or 6-membered hetero-monocyclic group containing one heteroatom, or a condensed heterocyclic group resulting from fusion of a benzene or cyclohexene ring with this heterocyclic ring. These benzene ring, heteromonocyclic group and condensed heterocyclic ring may preferably contain 1 to 2 substituents described above.

$R_1$ in general formula [I] is a monovalent hydrocarbon group or a monovalent heterocyclic group each of which may contain a substituent.

The hydrocarbon group $R_1$ may be aliphatic, alicyclic or aromatic. Examples of the hydrocarbon groups include alkyl groups having 1 to 20 carbon atoms, preferably 1 to 6 carbon atoms, such as methyl, ethyl, propyl and butyl groups; aryl groups having 6 to 14 carbon atoms such as phenyl, tolyl, xylyl and naphthyl groups; and aralkyl groups containing an alkylene group having 1 to 10, preferably 1 to 4, carbon atoms such as benzyl, phenylethyl, phenylpropyl and phenylbutyl groups.

The heterocyclic group $R_1$ is preferably a 5- or 6-membered hetero-monocyclic group containing 1 to 3, preferably 1 or 2, hetero atom of at least one kind such as a nitrogen, oxygen or sulfur atom, or a condensed heterocyclic group resulting from fusion of a benzene ring with the hetero-monocyclic group. Specific examples of the heterocyclic group are saturated heterocyclic groups such as saturated piperidine, piperazine, morpholine, pyrrolidine, indoline and couromane rings in addition to the examples of the unsaturated heterocyclic group given hereinabove with regard to the definition of

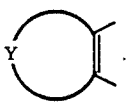

The hydrocarbon group or the heterocyclic group for $R_1$ may contain a substituent. $R_1$ preferably contains up to 5, preferably up to 3, substituents. Examples of the substituents may be the same as those given above with regard to

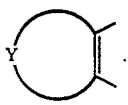

Examples of preferred groups $R_1$ include alkyl groups having 1 to 20 carbon atoms which may be substituted by a halogen atom, an alkoxy group having 1 to 4 carbon atoms or a phenyl group; aryl groups having 6 to 10 carbon atoms which may be substituted by a halogen atom or an alkoxy group having 1 to 4 carbon atoms; and 5- or 6-membered hetero-monocyclic groups containing 1 to 3 hetero atoms selected from nitrogen, oxygen and sulfur atoms (preferably one heteroatom), or condensed heterocyclic groups resulting from fusion of a benzene ring with the heterocyclic groups.

Alkyl groups having 1 to 6 carbon atoms, aralkyl groups having 7 to 10 carbon atoms or aryl groups having 6 to 10 carbon atoms are especially preferred as $R_1$.

In general formula [I],

is a norbornylidene or adamantylidene group which may have a substituent. The norbornylidene group is represented by the following formula.

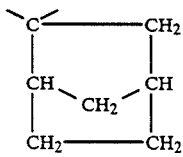

The adamantylidene group is represented by the following formula.

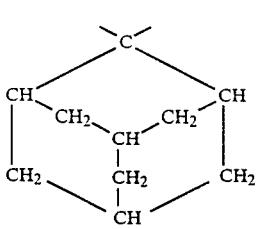

The above formulae show the skeletal structures of the norbornylidene group and the adamantylidene group having no substituent. One or more hydrogen atoms in the above formulae may be substituted by a substituent. The types and number of substituents and the substitution positions may be selected according to the purpose and utility. When the norbornylidene or adamantylidene group has a plurality of substituents, they may be of the same or different kinds.

Examples of the substituents for the norbornylidene or adamantylidene group include a hydroxyl group; alkylamino groups having 1 to 4 carbon atoms such as methylamino and diethylamino groups; alkoxy groups having 1 to 4 carbon atoms such as methoxy, ethoxy and tert-butoxy groups; aralkoxy groups having 7 to 15 carbon atoms such as a benzyloxy group; aryloxy groups having 6 to 14 carbon atoms such as phenoxy and 1-naphthoxy groups; lower alkyl groups having 1 to 4 carbon atoms such as methyl, ethyl and t-butyl groups; halogen atoms such as fluorine, chlorine and bromine atoms; a cyano group; a carboxyl group; alkoxycarbonyl groups having 2 to 10 carbon atoms such as an ethoxycarbonyl group; halogenated alkyl groups having 1 to 2 carbon atoms such as a trifluoromethyl group; a nitro group, aryl groups having 6 to 10 carbon atoms such as phenyl and tolyl groups; and aralkyl groups having 7 to 9 carbon atoms such as phenylethyl and phenylpropyl groups.

The halogen atoms, hydroxyl group, alkyl groups having 1 to 4 carbon atoms, alkoxy groups having 1 to 4 carbon atoms, alkoxycarbonyl groups having 2 to 10 carbon atoms, aralkyl groups having 7 to 9 carbon atoms and aryl groups having 6 to 10 carbon atoms are preferred.

In general formula [I] in this invention, X represents an oxygen atom (—O—), the group $>N-R_2$, the group $>N-A_1-B_1+A_2\!\!\!\xrightarrow{}_{\!\!m}\!\!(B_2\!\!\!\xrightarrow{}_{\!\!n}R_3$, the group $>N-A_3-A_4$ or the group $>N-A_3-R_4$. When

represents a norbornylidene group which may have a substituent, X is selected from the above atom and groups. But when it represents an adamantylidene group which may have a substituent, X is selected from the above groups other than the oxygen atom and the group $>N-R_2$. A compound in which

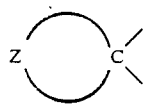

is an adamantylidene group and X is an oxygen atom or the group $>N-R_2$ is photochromic, but has low durability and cannot endure long-term use in actual applications.

When

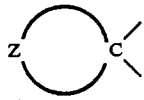

in general formula [I] is an adamantylidene group which may have a substituent, X is preferably the group >N—A$_1$—B$_1$—(A$_2$)$_m$(B$_2$)$_n$R$_3$, the group >N—A$_3$—A$_4$ or the group >N—A$_3$—R$_4$, particularly the group >N—A$_3$—R$_4$ or the group >N—A$_1$—B$_1$—(A$_2$)$_m$(B$_2$)$_n$R$_3$ (in which R$_3$ is an alkyl group having 1 to 10 carbon atoms which may be substituted by 1 to 3 atoms or groups selected from the class consisting of halogen atoms, a cyano group and a nitro group).

Most preferably, in general formula [I],

is a norbornylidene group which may have a substituent, and X is the group >N—A$_1$—B$_1$—(A$_2$)$_m$(B$_2$)$_n$R$_3$, the group >N—A$_3$—A$_4$ or the group >N—A$_3$—R$_4$, especially the group >N—A$_3$—R$_4$ or the group >N—A$_1$—B$_1$—(A$_2$)$_m$(B$_2$)$_n$R$_3$ (R$_3$ represents an alkyl group having 1 to 10 carbon atoms which may be substituted by 1 to 3 atoms or groups selected from the class consisting of halogen atoms, a cyano group and a nitro group).

Preferably, in general formula [I], X is the group >N—A$_1$—B$_1$—(A$_2$)$_m$(B$_2$)$_n$R$_3$ and R$_3$ is a naphthyl or naphthylalkyl group, or X is the group >N—A$_3$—A$_4$, the number of atoms in the main chain interposed between the naphthyl group and the imide group >N— is 3 to 7 because it leads to a compound having durable photochromism.

Now, the definitions of R$_2$, R$_3$, R$_4$, A$_1$, A$_2$, A$_3$, A$_4$, B$_1$, B$_2$, m and n in X will be described.

R$_2$ represents a hydrogen atom, an alkyl group having 1 to 20 carbon atoms, or an aryl group having 6 to 10 carbon atoms. Examples of the alkyl group are methyl, ethyl, n-, iso- or tert-butyl, pentyl, hexyl, octyl and decyl groups. Those having 1 to 10 carbon atoms are preferred. Examples of the aryl group are phenyl, tolyl and naphthyl groups.

A$_1$ and A$_2$ may be identical or different, and each may represent an alkylene group having 1 to 10 carbon atoms, an alkylidene group having 2 to 10 carbon atoms, a cycloalkylene group having 3 to 10 carbon atoms, or an alkylcycloalkanediyl group having 6 to 10 carbon atoms. Specific examples of the alkylene groups are methylene, ethylene, propylene, butylene, trimethylene, tetramethylene and 2,2-dimethyltrimethylene groups. Specific examples of the alkylidene groups are ethylidene, propylidene and isopropylidene groups. A cyclohexylene group may be cited as the example of the cycloalkylene groups. Examples of the alkylcycloalkanediyl groups are 2-methylcyclohexane-α,1-diyl

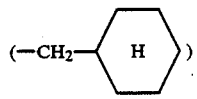

and 4-methylcyclohexane-α,1-diyl

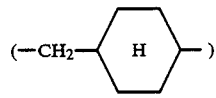

groups. The alkylene groups having 1 to 6 carbon atoms, the alkylidene groups having 2 to 6 carbon atoms, the cycloalkylene groups having 3 to 6 carbon atoms, and the alkylcycloalkanediyl groups having 6 to 7 carbon atoms are preferred as A$_1$ and A$_2$.

B$_1$ and B$_2$ may be identical or different, and each is selected from the following seven bridging groups.

$$-O-, \quad -\overset{O}{\underset{\|}{C}}-, \quad -O\overset{O}{\underset{\|}{C}}-, \quad -\overset{O}{\underset{\|}{C}}O-,$$

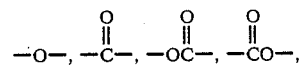

m and n, independently from each other, represent 0 or 1. When they represent 0, —(A$_2$)$_m$ or —(B$_2$)$_n$ means a bond. When m is 0, n is also 0.

R$_3$ represents an alkyl group having 1 to 10 carbon atoms, a naphthyl group, or a naphthylalkyl group having 1 to 4 carbon atoms in the alkyl moiety. The alkyl group having 1 to 10 carbon atoms above may be substituted by 1 to 3 atoms or groups selected from the class consisting of halogen atoms, a cyano group and a nitro group. The naphthyl and naphthylalkyl group may be substituted by 1 to 3 atoms or groups selected from the class consisting of halogen atoms, a cyano group, a nitro group, alkylamino groups having 1 to 3 carbon atoms, alkyl groups having 1 to 3 carbon atoms and alkoxy groups having 1 to 3 carbon atoms. Examples of the alkyl groups having 1 to 10 carbon atoms may be the same as those given with regard to the alkyl groups for R$_2$. Examples of the naphthylalkyl group are naphthylmethyl, naphthylethyl, naphthylpropyl and naphthylbutyl groups.

A$_3$ represents an alkylene group having 1 to 10 carbon atoms, an alkylidene group having 2 to 10 carbon atoms, a cycloalkylene group having 3 to 10 carbon atoms, or an alkylcycloalkanediyl group having 6 to 10 carbon atoms. Specific examples of the alkylene, alkylidene, cycloalkylene and aikylcycloalkanediyl groups may be the same as those given with regard to A$_1$ and A$_2$ above.

A$_4$ represents a naphthyl group which may be substituted by 1 to 3 atoms or groups selected from the class consisting of halogen atoms, cyano groups, nitro groups, alkylamino groups having 1 to 3 carbon atoms, alkyl groups having 1 to 3 carbon atoms and alkoxy groups having 1 to 3 carbon atoms.

$R_4$ represents a halogen atom, a cyano group or a nitro group.

In the definitions of $R_3$ and $A_4$, the halogen atom may be, for example, fluorine, chlorine or bromine.

The compound of general formula [I] generally exists as a pale yellow solid at room temperature, and can generally be identified by the following procedures (a) to (c).

(a) The types and number of protons existing in the molecule can be determined by measuring the proton nuclear magnetic resonance spectrum ($H^1$-NMR) of the compound. Specifically, in the $H^1$-NMR spectrum, there appear a peak based on aromatic protons near $\delta$7-8 ppm, a broad peak based on protons derived from the adamantylidene or norbornylidene group near $\delta$1.2-2.5 ppm, and a peak based on the alkyl group in $R_1$ near $\delta$1.2-4.0 ppm (where $R_1$ is an alkyl group). By comparing the $\delta$ peak intensities of these peaks, the number of protons of the bonding groups can be determined.

(b) By elemental analysis, the weight percentages of carbon, hydrogen, nitrogen, sulfur and halogen can be determined. The weight percent of oxygen can be calculated by subtracting the total weight percentage of the elements from 100. Accordingly, the composition of the product can be determined.

(c) The types of carbons present in the molecule can be determined by measuring the $^{13}$C-nuclear magnetic resonance spectrum of the compound. There appear a peak derived from carbons of the adamantylidene or norbornylidene group near $\delta$27-52 ppm, a peak based on carbons of the alkyl group in $R_1$ near $\delta$15-35 ppm (where $R_1$ is an alkyl group), a peak based on the carbons of the aromatic hydrocarbon group or the unsaturated heterocyclic group near $\delta$110 to 150 ppm, and a peak based on the carbon of $>$C=O near $\delta$160-170 ppm.

The compound of general formula [I] may be produced by any manufacturing process, and is not limited by the type of manufacturing process. Preferred typical processes are described below without any intention of limiting the invention thereby.

PROCESS A

A process for producing a compound represented by the following general formula (I)

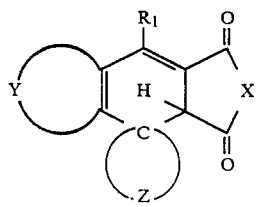

wherein

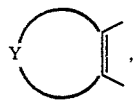

and X are as defined hereinabove,
which comprises cyclizing a compound represented by the following general formula [II]

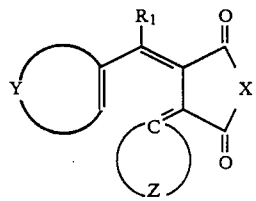

or reacting the compound of general formula [II] with an amine compound represented by the following general formula [III-a], [III-b], [III-c] or [III-d]

  [III-a]

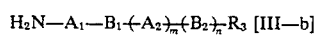  [III-b]

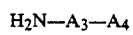  [III-c]

  [III-d]

wherein $R_2$, $R_3$, $R_4$, $A_1$, $A_2$, $A_3$, $A_4$, $B_1$, $B_2$, m and n are as defined above,
and then cyclizing the reaction product.

A compound of general formula [I] in which X is an oxygen atom is obtained by cyclizing the acid anhydride of general formula [II] in process A. Compounds of general formula [I] containing an imide ring in which X is other than oxygen can be obtained by reacting the acid anhydride of general formula [II] with the amine compound of formula [III-a], [III-b], [III-c] or [III-d], and then cyclizing the resulting product.

The reaction in process A is carried out preferably in a solvent. The solvent may be an aprotic polar solvent such as N-methylpyrrolidone, dimethylformamide, tetrahydrofuran or 1,4-dioxane.

The direct cyclization of the acid anhydride of general formula [II] and the cyclization of the reaction product of the acid anhydride with the amine compound can be carried out under the same conditions. The cyclization is carried out, for example, by heating the compound to a temperature of 160° to 220° C., or carrying out this heating with ultraviolet irradiation, or by bringing the compound into contact with a Lewis acid catalyst. The Lewis acid catalyst may be a known compound such as $SnCl_4$, $TiCl_4$, $SbCl_5$ and $AlCl_3$. The amount of the Lewis acid used is not particularly restricted, but usually amounts of 0.001 to 1 mole per mole of the compound to be cyclized are preferred.

In the reaction of the acid anhydride of general formula [II] with the amine compound of general formula [III-a], [III-b], [III-c] or [III-d], the mole ratio of the acid anhydride to the amine compound can be varied over a wide range, but is generally from 1:10 to 10:1, preferably from 1:5 to 5:1. This reaction is carried out usually at a temperature of 25° to 160° C. for a period of 1 to 24 hours. After the reaction, the solvent is removed, and the product is dehydrated with a dehydrating agent such as acetyl chloride and acetic anhydride. By cyclizing the resulting compound under the conditions described above, the compound [I] of the invention can be obtained.

The acid anhydride of general formula [II] used as the starting material in process A can be obtained, for example, by condensing a carbonyl compound represented by the following general formula [II-a]

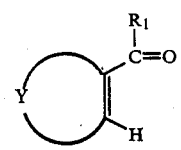

[II-a]

wherein

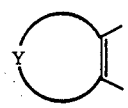

and $R_1$ are as defined with regard to general formula [I], with a succinic diester derivative represented by the following general formula [II-b]

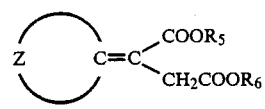

[II-b]

wherein

is as defined in general formula [I], and $R_5$ and $R_6$ are identical or different and represent an alkyl group having 1 to 6 carbon atoms, and treating the resulting product in a manner described below.

The mole ratio of the carbonyl compound to the succinic diester derivative in the above condensation reaction may be varied over a wide range, and is generally from 1:10 to 10:1, preferably 1:5 to 5:1. The reaction is carried out at a temperature of 0° to 110° C., preferably 10° to 100° C. The reaction is suitably carried out in a solvent. The solvent is desirably an aprotic solvent such as benzene, diethyl ether, toluene and tetrahydrofuran.

Generally, the condensation is carried out in the presence of a condensing agent such as sodium hydride, potassium t-butoxide and sodium ethylate. The condensing agent may be used usually in an amount of 0.1 to 10 moles per mole of the carbonyl compound of general formula [II-a].

After the reaction, the resulting dicarboxylic acid diester is converted to the free dicarboxylic acid. This reaction is carried out by using known hydrolysis reaction conditions in the presence of bases. For example, the reaction is carried out at 0° to 80° C. using a 10% ethanolic aqueous solution of sodium hydroxide.

The resulting dicarboxylic acid can be converted to the acid anhydride of general formula [II] by known methods. Conversion into the acid anhydride may be carried out, for example, by using a well known reagent such as acetic anhydride or acetyl chloride.

PROCESS B

A process for producing a compound represented by the general formula [I]

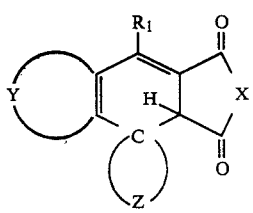

[I]

wherein

$R_1$,

and X are as defined with regard to general formula [I], provided that an oxygen atom is excluded from the above definition of X, which comprises reacting an imide compound represented by the following general formula [IV]

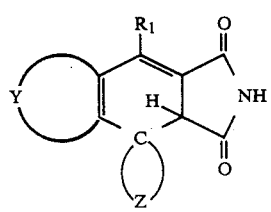

[IV]

wherein

$R_1$ and

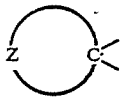

are as defined with regard to general formula [I], with an alkali metal, and then reacting the product with a bromine compound represented by the following general formula [V-a], [V-b], [V-c] or [V-d]

  [V-a]

  [V-b]

  [V-c]

  [V-d]

wherein $R_2$, $R_3$, $R_4$, $A_1$, $A_2$, $A_3$, $A_4$, $B_1$, $B_2$, m and n are as defined with regard to general formula [I].

Examples of the alkali metal used in process B are sodium, potassium and lithium. The amount of the alkali metal to be reacted is generally 1.0 to 10 moles per mole of the compound of general formula [IV]. Preferably, the amount of the bromine compound of general formula [V-a], [V-b], [V-c], or [V-d] is generally 0.5 to 10 moles per mole of the compound [IV] obtained by reaction with the alkali metal.

The solvent used in this process may be any of those which are described above with regard to process A. Usually, the reaction temperature used may preferably be 0° to 100° C. The compound of general formula [I] of the invention can be obtained by the above processes A and B or by modifications of these processes.

The compound of general formula [I] has a photochromic action and excellent durability. By using it in combination with an ultraviolet stabilizer, the durability of the photochromic action of compound [I] can be further enhanced. Accordingly, it is advantageous to use the compound [I] of the invention in combination with an ultraviolet stabilizer.

The ultraviolet stabilizer used for this purpose may be any of those known as additives to various plastics. If the durability of the compound [I] is considered, light extinguishers for oxygen in the singlet state and hindered amine light stabilizers can be suitably used as the ultraviolet stabilizer.

Examples of light extinguishers for oxygen in the singlet state which can be suitably used in this invention include a complex of $Ni^{2+}$ and an organic ligand, cobalt (III) tris-di-n-butyldithiocarbamate, iron (III) diisopropyldithiocarbamate and cobalt (II) diisopropyldithiocarbamate. The complex of $Ni^{2+}$ and an organic ligand is especially preferred. Examples of this complex are shown below.

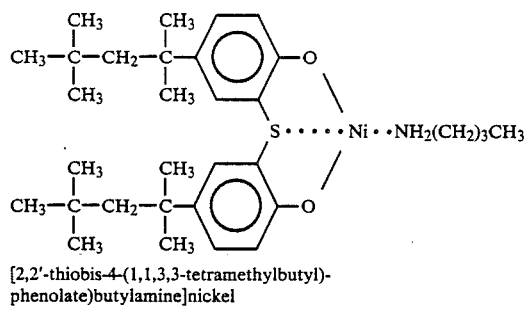

[2,2'-thiobis-4-(1,1,3,3-tetramethylbutyl)-phenolate)butylamine]nickel

U-1

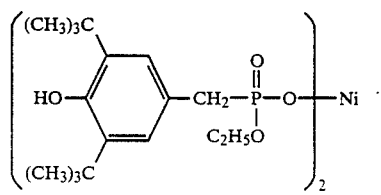

Nickel-bis[o-ethyl(3,5-di-tert-butyl-4-hydroxybenzyl)]phosphonate

U-2

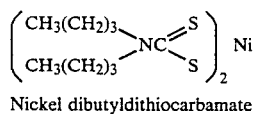

Nickel dibutyldithiocarbamate

U-3

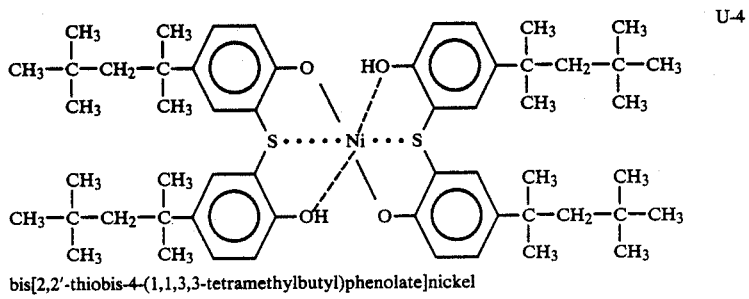

bis[2,2'-thiobis-4-(1,1,3,3-tetramethylbutyl)phenolate]nickel

There may also be cited Ni complexes sold by Ferro Corporation under the tradenames UV-Chek AM105, UV-Chek AM126 and UV-Chek AM205.

Specific examples of the hindered amine light stabilizers suitable as the ultraviolet stabilizer are given below.

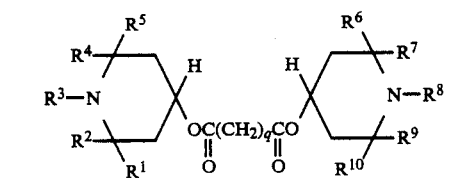

U-5

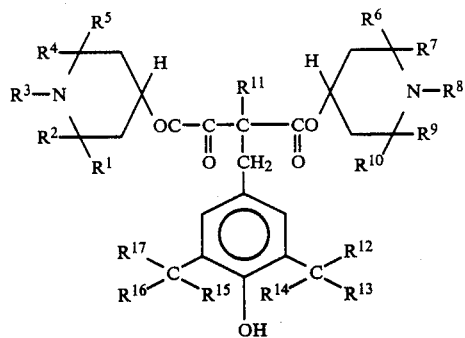

U-6

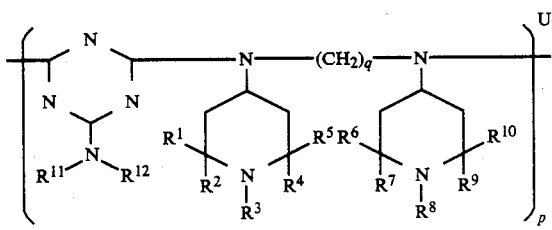

U-7

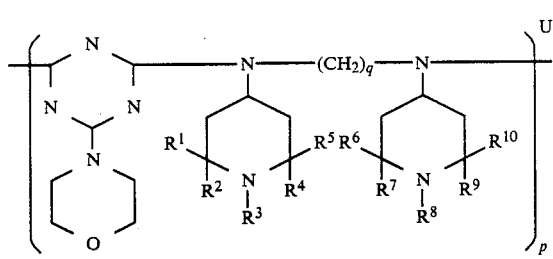

U-8

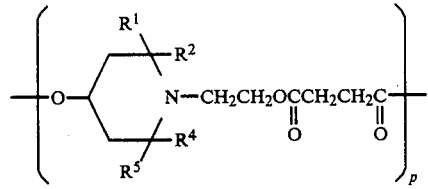

U-9

$(C_{26}H_{52}N_4)_p$     U-10

In the formulae U-5 to U-10, $R^1$, $R^2$, $R^4$, $R^5$, $R^6$, $R^7$, $R^9$, $R^{10}$, $R^{11}$, $R^{12}$, $R^{13}$, $R^{14}$, $R^{15}$, $R^{16}$ and $R^{17}$ represent an alkyl group, $R^3$ and $R^8$ represent a hydrogen atom or an alkyl group, and p and q are positive integers.

The alkyl groups in U-5 to U-9 are not particularly limited in the number of carbons. Generally, the alkyl groups preferably have 1 to 12 carbon atoms because of the ease of obtaining these compounds.

Sumisorb LS-2000 and LS-2001 (tradenames of Sumitomo Chemical Co., Ltd.) may also be cited as examples of the hindered amine light stabilizer.

Ultraviolet stabilizers of formulae U-1, U-3, U-5, U-6, U-8 and U-9 can be preferably used for increasing the durability of the photochromic actions of the compounds of general formula [I].

The mixing ratio of the compound of formula [I] and the ultraviolet stabilizer can be selected from a wide range. Generally, if the durability of a composition of the compound [I] and the ultraviolet stabilizer and the prevention of dissolution of the components, the proportion of the ultraviolet stabilizer is generally 0.01 to 10,000 parts by weight, more preferably 50 to 400 parts by weight, per 100 parts by weight of the compound [I].

The compound of general formula [I] provided by this invention is well soluble in general organic solvents such as toluene, chloroform and tetrahydrofuran. When the compound [I] is dissolved in such a solvent, the solution has a reversible photochromic action such that it is almost colorless and transparent, and when sunlight or ultraviolet rays are irradiated onto it, it develops a color, and when the light is shut off, it rapidly attains the original colorless form. The compound of formula [I] also exhibits this photochromic action in a polymeric solid matrix with a reversing speed on the order of seconds. A high-molecular-weight polymer for forming such a polymeric material may be any polymer in which the compound [I] is dispersible uniformly. The molecular weight of the high-molecular-weight polymer is selected from 500 to 500,000. Examples of optically desirable polymers include polymethyl acrylate, polyethyl acrylate, polymethyl methacrylate, polyethyl methacrylate, polystyrene, polyacrylonitrile, polyvinyl alcohol, polyacrylamide, poly(2-hydroxyethyl methacrylate), polydimethylsiloxane, polycarbonate and poly(allyl diglycol carbonate); and copolymers obtained by copolymerizing the monomers constituting the above polymers either with each other or with other monomers.

The amount of the compound [I] to be dispersed in the above high-molecular polymer is generally 0.001 to 70 parts by weight, preferably 0.005 to 30 parts by weight, especially preferably 0.1 to 15 parts by weight, per 100 parts by weight of the high-molecular polymer. When the ultraviolet stabilizer is used by mixing it with the high-molecular polymer, its amount may be within the range of the mixing proportion with respect to the compound [I] described above.

The photochromic action of the compound of general formula [I] has much higher durability than known fulgimide compounds.

Accordingly, the compounds of this invention can be broadly utilized as a photochromic material. For example, they can be utilized in various recording materials superseding silver salt photographic materials, for example in memory materials, printing photographic materials, recording materials for a cathode ray tube, photographic materials for laser and photographic materials for holography. The photochromic material containing the compound of this invention can also be utilized as a photochromic lens material, an optical filter material, a display material, an actinometer, or a decorative material. For example, a photochromic lens may be produced by any method which can give uniform light adjusting properties. Specifically, a polymer film in which the photochromic compound of this invention is uniformly dispersed is sandwiched between lenses. Alternatively, a photochromic lens may be produced by dissolving the compound of the invention in a silicone oil, impregnating the solution in the surface of a lens at 150° to 200° C. over 10 to 60 minutes, and coating the surface with a curable substance. It is also possible to coat the above polymer film on the surface of a lens and coating the surface with a curable substance to provide a photochromic lens. A photochromic lens may also be produced by dispersing the compound of the invention in monomers capable of forming an organic lens, and then polymerizing and curing the monomeric mixture.

In a solid polymer matrix, the compound of general formula [I] provided by the invention hardly undergoes effect by the type of the matrix. In a general condition, it is stably colorless, but upon irradiation of ultraviolet rays, immediately develops a color. When the ultraviolet irradiation is stopped, the compound returns to its original colorless form within a time on the order of seconds. The compound has the property of repeating this color change with good durability.

BRIEF DESCRIPTION OF THE DRAWINGS

FIG. 1 is the proton nuclear magnetic resonance spectrum of the product obtained in Example 1;

FIG. 2 is the proton nuclear magnetic resonance spectrum of the product obtained in Example 2.

Figure 3:
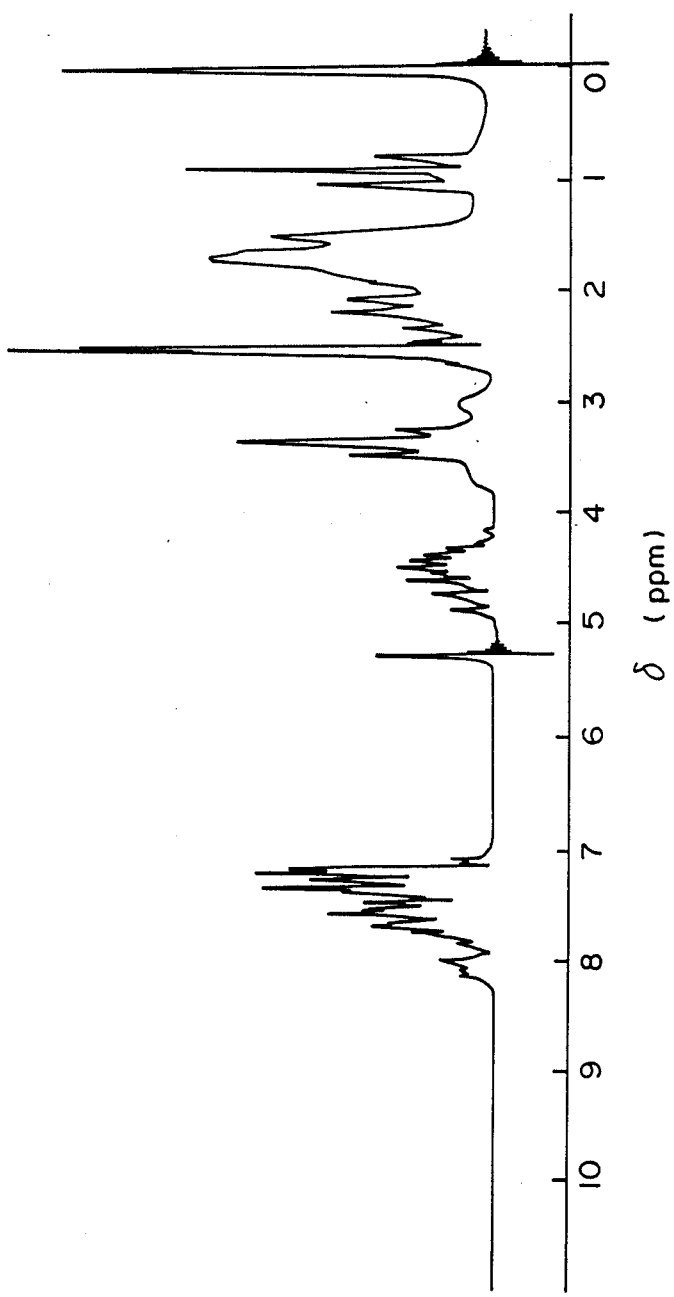
FIG. 3 is the proton nuclear magnetic resonance spectrum of the product obtained in Example 5.

The following examples illustrate the present invention in greater detail without limiting the invention thereby.

In the Examples, the following ultraviolt stabilizers were used.

Cyasorb UV1084 (tradename; produced by American cyanamid Co.)

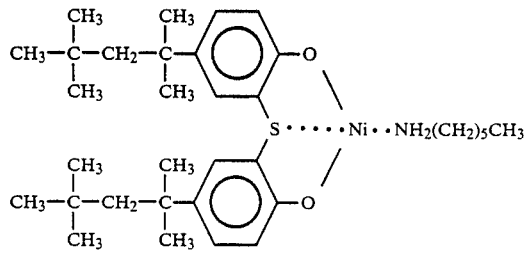

Irganostab 2002 (tradename produced by Ciba-Geigy Co.)

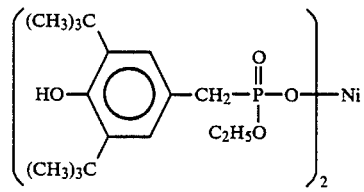

Rylex NBC (tradename, produced by E. I. du Pont de Nemours & Co.)

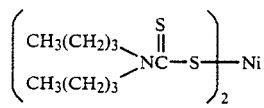

UV-Chek AM101 (tradename, produced by Ferro Corporation)

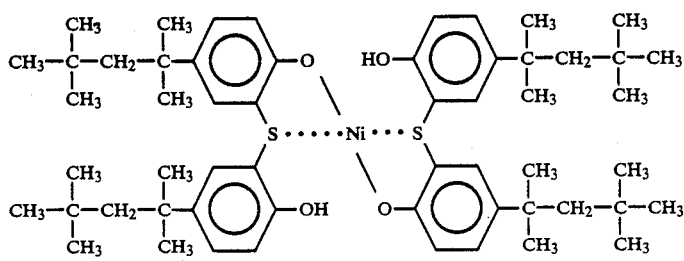
UV-Chek AM105 (tradename, produced by Ferro Corporation)
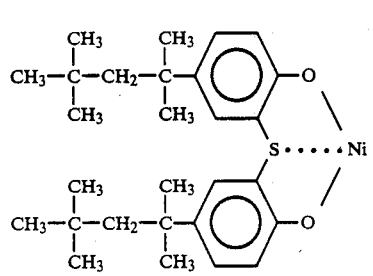
Tinuvin 770 (tradename, produced by Chiba-Geigy Co.)
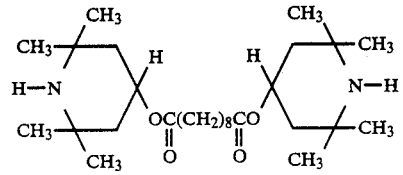
Tinuvin 765 (tradename, produced by Ciba-Geigy Co.)
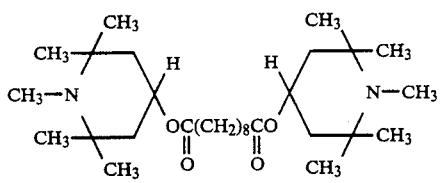
Tinuvin 144 (tradename, produced by Chiba-Geigy Co.)
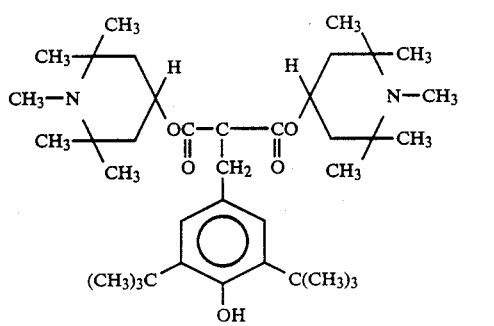
Chimasorb 994 (tradename, produced by Ciba-Geigy Co.)
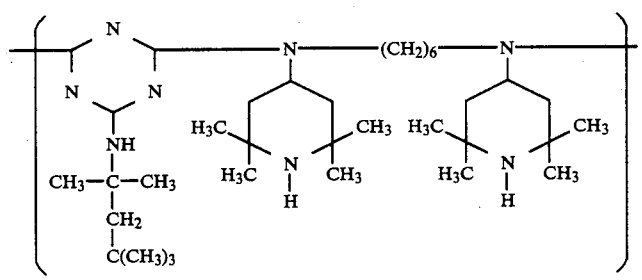
Cyasorb 3346 (tradename, produced by American Cyanamid Cmpany)
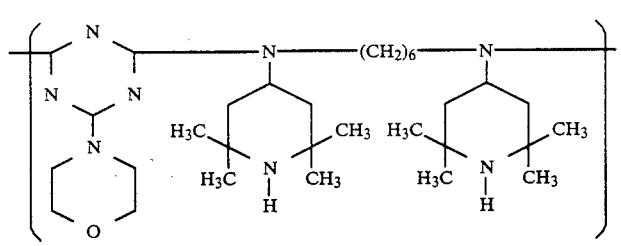

Tinuvin 622 (tradename, a produced by Ciba-Geigy Co.)

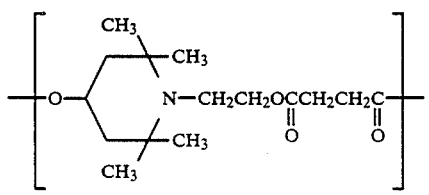

Spinuvex A-56 (tradename, produced by Borg Warner Corp.)

EXAMPLE 1

3.4 g (0.01 mole) of 3-thienylethylidene-2-adamantylidene succinic anhydride of the following formula

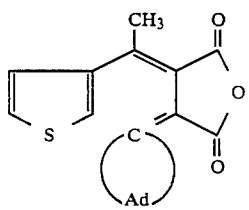

and 17.8 g (0.02 mole) of glycine methyl ester of the following formula

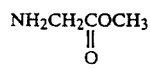

were dissolved in toluene, and the solution was heated at 50° C. for 2 hours in a nitrogen atmosphere. After the reaction, the solvent was removed, and the residue was dissolved in acetyl chloride. The solution was refluxed for 1 hour to cyclize the reaction product. The resulting compound was refluxed for 6 hours in o-dichlorobenzene to convert it into a compound of formula (I). This compound was purified by chromatography on a silica gel column using benzene and ether as an eluent. Recrystallization from chloroform and hexane gave pale yellow needles in a yield of 27%. The elemental analysis values of this compound were C 66.79%, H 6.09%, N 3.36%, O 15.8% and S 7.96%, which well agreed with the calculated values for $C_{23}H_{25}O_4NS$ (C 67.15%, H 6.08%, N 3.41%, O 15.6%, and S 7.79%). The proton nuclear magnetic resonance spectrum of the resulting compound was taken and shown in FIG. 1. The proton nuclear magnetic resonance spectrum of the resulting compound showed a peak of 2H based on aromatic protons near $\delta 7.0$-$8.0$ ppm, a peak of 3H based on the protons of the >C—CH₃ bond at $\delta 2.7$ ppm, a peak of 3H based on the methyl protons of the

bond near $\delta 3.7$ ppm, a peak of 14H based on the protons of the adamantylidene group at $\delta 1.2$-$2.5$ ppm, and a peak of 3H based on the 1-5 shifted proton and the >N—CH₂— bond at $\delta 3$-$5$ ppm.

The ¹³C-nuclear magnetic resonance spectrum of the resulting product was measured. It showed a peak based on the carbons of the adamantylidene group and the carbon of the methylene chain at $\delta 27$-$70$ ppm, a peak based on the carbon of the methyl group near $\delta 15.6$ ppm, a peak based on the carbons of the thiophene ring near $\delta 110$-$160$ ppm, and a peak based on the carbon of the >C═O bond near $\delta 160$-$170$ ppm.

From the above results, the isolated products was determined to be a compound of the following structural formula.

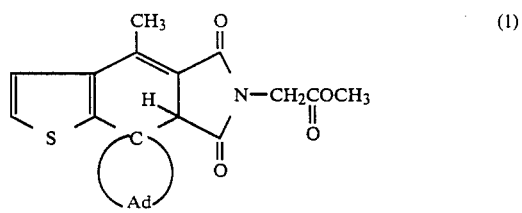

EXAMPLE 2

3.4 g (0.01 mole) of a compound of the following formula

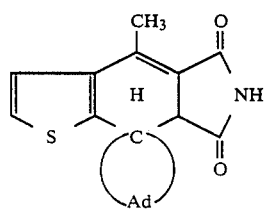

was dissolved in tetrahydrofuran, and then reacted with 1 g of metallic potassium at room temperature to give 3 g of potassium imide of the following formula.

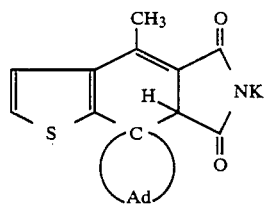

This compound was reacted with 1.2 g (0.01 mole) of bromoacetonitrile BrCH₂CN in dimethylformamide to give a fulgimide compound (2) shown below. This compound was purified by chromatography on silica gel using chloroform and hexane as an eluent and was obtained in a field of 57% as pale yellow crystals by recrystallization from hexane. This compound had the following elemental analysis values: C 69.81%; H 5.80%; N 7.44%; O 8.50%; S 8.46%. These values well agreed with the calculated values for $C_{22}H_{22}N_2O_2S$ (C 69.84%; H 5.82%; N 7.41%; O 8.47%; S 8.47%). The proton nuclear magnetic resonance spectrum (FIG. 2) of the resulting compound was measured. The spectrum showed a peak of 2H based on the protons of the thiophene ring near δ7.0–7.5 ppm, a peak of 2H based on the protons of >N—CH₂CN bond near δ4.5 ppm, a peak of 1H based on the 1–5 shifted proton near δ3.7 ppm, a peak of 3H based on the protons of —CH₃ bond near δ2.7 ppm, and a peak of 14H based on the protons of the —CH₂— bond and the protons based on the adamantylidene group near δ1.3–2.5 ppm.

The $^{13}$-NMR of the resulting compound was also measured. The spectrum showed a peak based on the carbons of the adamantylidene group near δ27–70 ppm, a peak based on the methyl carbon near δ15.6 ppm, a peak based on the carbons of the thiophene ring near δ110–160 ppm, and a peak based on the carbon of >C=O bond near δ160–170 ppm.

From the above results, the isolated product was determined to be a fulgimide compound (2) of the following structural formula.

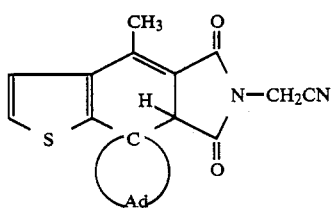
(2)

EXAMPLE 3

Ten grams (0.049 mole) of 5-bromo-3-acetylthiophene and 16.9 g (0.064 mole) of diethyl norbornylidenesuccinate of the following formula

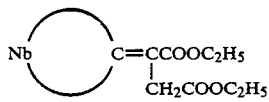

were dissolved in 200 cc of toluene to prepare a solution. In an atmosphere of nitrogen, the solution was added dropwise over the course of 3 hours to a solution of 5 g of sodium hydride in 200 cc of toluene so that the temperature of the toluene solution became 0° C. or below. After the addition, the mixture was maintained at 0° C. or below, and vigorously stirred for 10 hours. The product was hydrolyzed with an excessive amount of a 10% alcoholic aqueous solution of potassium hydroxide, and then the hydrolysis product was acidified with hydrochloric acid. The resulting dicarboxylic acid was treated with 100 cc of acetyl chloride, and purified by chromatography on silica gel to give 10.2 g of a fulgide compound of the following formula.

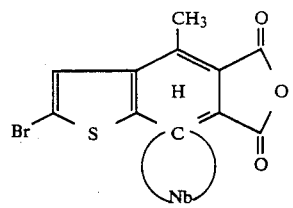

Four grams (0.01 mole) of the above compound and 3.5 g (0.02 mole) of 2-naphthylethylamine of the following formula

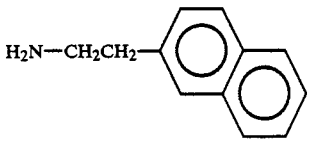

were dissolved in toluene, and heated at 50° C. for 2 hours in an atmosphere of nitrogen. After the reaction, the solvent was removed, and the residue was dissolved in acetyl chloride, and refluxed for 1 hour to cyclize the product obtained above. The resulting compound was refluxed for 6 hours in o-dichlorobenzene to form a compound (3) shown below. The compound was purified by chromatography on silica gel using benzene and ether as an eluent. By recrystallization from chloroform and hexane, it was obtained as yellow needles (melting point 142°–143° C.) in a yield of 20%. The elemental analysis values of this compound were C 65.50%, H 4.85%, Br 14.98%, N 2.65%, O 6.01%, and S 6.01%, which well agreed with the calculated values for $C_{29}H_{26}BrNO_2S$ (C 65.42%, H 4.89%, Br 15.02%, N 2.63%, O 6.02% and S 6.03%). The proton nuclear magnetic resonance spectrum of the resulting compound was measured. The spectrum showed a peak of 8H based on aromatic protons near δ7.0–8.0 ppm, a proton of 3H based on the 1–5 shifted proton and based on the protons of >N—CH₂— near δ3.8 ppm, a proton of 3H based on the protons of the >C—CH₃ bond near δ2.7 ppm, and a peak of 19H based on the protons of the —CH₂— bond and the protons of the norbornylidene group near δ1.3–2.5 ppm.

The $^{13}$C-nuclear magnetic resonance spectrum of the resulting compound is also measured. The spectrum showed a peak based on the carbons of the norbornylidene group and the carbon of the methylene chain near δ27–52 ppm, a peak based on the carbon of the methyl group near δ15.6 ppm, a peak based on the carbons of the napthalene ring and the carbons of the thiophene ring near δ110–160 ppm, and a peak based on the carbon of the >C=O bond near δ160—170 ppm.

From the above results, the isolated product was determined to be a fulgimide compound (3) of the following structural formula.

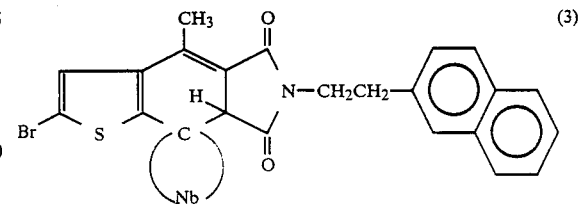
(3)

EXAMPLE 4

A fulgimide compound of the following structural formula was obtained by repeating Example 3 except that NH₃ was used instead of 2-naphthylethylamine.

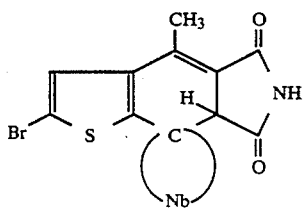

Six grams (0.15 mole) of this compound was dissolved in tetrahydrofuran, and reacted with metallic sodium at room temperature to give 5 g of an imide sodium of the following formula.

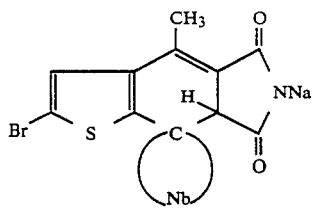

This compound was reacted with 2 g (0.01 mole) of 2-bromoethyl 2-naphthoxyacetate of the following formula

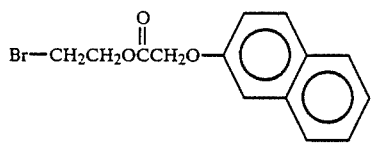

in dimethylformamide to give a flugimide compound (4) shown below. This compound was purified by chromatography on silica gel using chloroform and hexane as an eluent, and from hexane, it was obtained as yellow needles (melting point 123°–125° C.) in a yield of 53%.

The resulting compound had elemental analysis values C 64.99%, H 4.70%, Br 13.87%, N 2.42%, and O 14.02%, which well agreed with the calculated values for $C_{31}H_{27}BrNO_5$ (C 64.93%, H 4.71%, Br 13.95%, N 2.44%, and O 13.96%).

The proton NMR spectrum of the resulting compound was measured. The spectrum showed a peak of 8H based on the aromatic protons near δ7.0 to 8.0 ppm, a peak of 7H based on the protons of the —CH$_2$— bond and the 1–5 shifted proton near δ3.0–5.0 ppm, a peak of 3H based on the —CH$_3$ bond near δ2.7 ppm, and a peak of 10H based on the norbornylidene group at δ1.0–2.2 ppm.

The $^{13}$C-NMR spectrum of the resulting comound was also measured. The spectrum showed a peak based on the carbons of the norbornylidene group and the carbon of the methylene chain near δ27–52 ppm, a peak based on the carbon of the methyl group near δ15.6 ppm, a peak based on the carbons of the thiophene ring and the carbons of the naphthalene ring near δ100–160 ppm, and a peak based on the carbon of the >C=O bond near δ160–170 ppm.

From the foregoing results, the isolated product was determined to be a fulgimide compound (4) of the following formula.

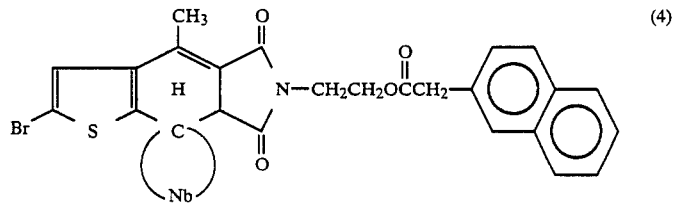

EXAMPLE 5

3.4 g (0.01 mole) of 3-thienylethylidene-2-adamantylidene succinic anhydride of the following formula

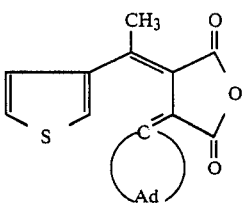

and 2.1 g (0.02 mole) of 2-naphthylethyl 2-aminobutyrate of the following formula

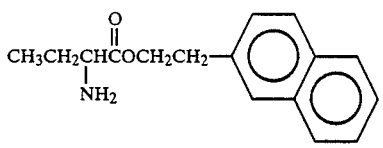

were dissolved in toluene, and heated at 50° C. for 2 hours in an atmosphere of nitrogen. After the reaction, the solvent was removed, and the residue was dissolved in acetyl chloride and refluxed for 1 hour to cyclize the above reaction product. The resulting compound was refluxed for 6 hours in o-dichlorobenzene to form a fulgimide compound (5) of the following structure. This compound was purified by chromatography on silica gel using benzene and ether as an eluent. By recrystallization from chloroform and hexane, it was obtained as yellow needles (melting point 120°–123° C.) in a yield of 27%.

The elemental analysis values of the resulting compound were C 74.63%, H 6.36%, N 2.43%, O 11.08%, and S 5.50%, which well agreed with the calculated values for $C_{36}H_{37}O_4NS$ (C 74.61%, H 6.39%, N 2.42%, O 11.5%, and S 5.53%).

The proton NMR spectrum (FIG. 3) of the resulting compound was measured. The spectrum showed a peak of 9H based on aromatic protons near δ7.0–8.0 ppm, a peak of 3H based on the protons of the >C—CH$_3$ bond at δ2.7 ppm, a peak of 3H based on the protons of the methyl group in the —CH₂—CH₃ bond at δ0.8-1.2 ppm, a peak of 16H based on the protons of the —CH₂— bond and the adamantylidene group at δ1.2-2.5 ppm, and a peak of 7H based on the 1-5 shifted proton and the —CH₂— bond at δ3-5 ppm.

The $^{13}$C-NMR spectrum of the resulting compound was also measured. The spectrum showed a peak based on the carbons of the adamantylidene group and the carbon of the methyl group, a peak based on the carbons of the thiophene group and the carbons of the naphthyl group near δ110-160 ppm, and a peak based on the carbon of the >C=O bond near δ160-170 ppm.

From the above results, the isolated products was determined to be a fulgimide compound (5) of the following structure.

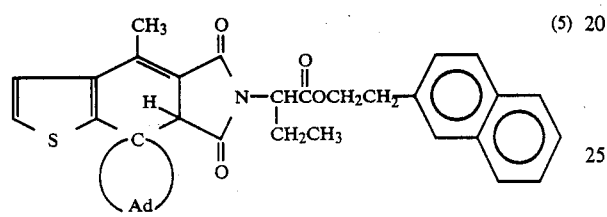

(5)

EXAMPLE 6

3.4 g (0.01 mole) of a fulgimide compound of the following formula

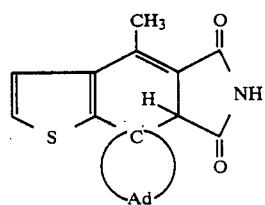

was dissolved in tetrahydrofuran, and reacted with 1 g of metallic potassium at room temperature to give 3 g of imide potassium of the following formula.

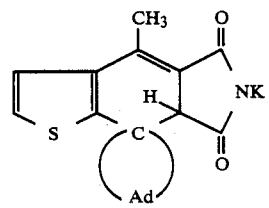

The resulting compound and 1.8 g (0.01 mole) of 1-naphthylethyl 5-bromovalerate of the following formula

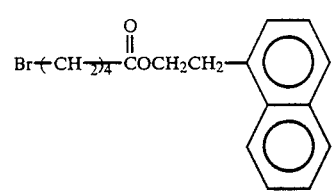

were reacted in dimethylformamide to give a fulgimide compound (6) shown below. This compound was purified by chromatography on silica gel using chloroform and hexane as an eluent. By recrystallization from hexane, it was obtained as yellow crystals (melting point 117°-119° C.) in a yield of 57%.

The elemental analysis values of the resulting compounds were C 74.65%, H 6.61%, N 2.39%, O 10.93%, and S 5.42%, which well agreed with the calculated values for C₃₇H₃₉NO₄S (C 74.87%, H 6.58%, N 2.36%, O 10.79% and S 5.40%).

The proton NMR spectrum of the resulting compound was measured. The spectrum showed a peak of 9H based on aromatic protons near δ7.0-8.0 ppm, a peak of 2H based on the protons of the

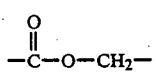

bond near δ4.4 ppm, a peak of 3H based on the 1-5 shifted proton and protons of the >N—CH₂— bond near δ3.7 ppm, a peak of 3H based on the protons of —CH₃ bond near δ2.7 ppm, and a peak of 22H based on the protons of —CH₂— bond and the protons based on the adamantylidene group near δ1.3-2.5 ppm.

The $^{13}$C-NMR spectrum of the resulting compound was also measured. The spectrum showed a peak based on the carbons of the adamantylidene group and the carbon of the methylene chain near δ27-52 ppm, a peak based on the carbon of the methyl group near δ15.6 ppm, a peak based on the carbons of the thiophene ring and the carbons of the naphthalene ring near δ110-160 ppm, and a peak based on the carbon of the >C=O bond near δ160-170 ppm.

From the above results, the isolated product was determined to be a fulgimide compound (6) of the following structure.

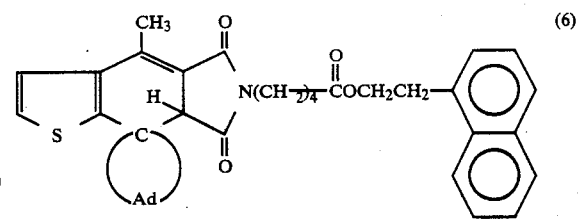

(6)

EXAMPLE 7

Ten grams (0.049 mole) of 5-bromo-3-acetylthiophene and 16.9 g (0.064 mole) of diethylnorbornylidenesuccinate of the following formula

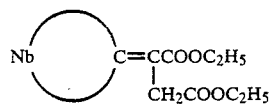

were dissolved in 200 cc of toluene to form a solution. The toluene solution was added dropwise over 3 hours in an atmosphere of nitrogen to a solution of 5 g of sodium hydride in 200 cc of toluene so that the temperature of the toluene solution became 0° C. or below. After the addition, the mixture was vigorously stirred for 10 hours while the liquid temperature was maintained at 0° C. or below. The mixture was hydrolyzed with an excessive amount of a 10% alcoholic aqueous solution of potassium hydroxide and acidified with hydrochloric acid. The resulting dicarboxylic acid was treated with 100 cc of acetyl chloride, and purified by chromatography on silica gel to give 10.2 g of a fulgide compound of the following formula.

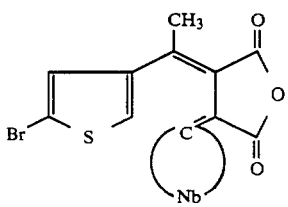

The resulting compound was refluxed in o-dichlorobenzene for 8 hours to rearrange it to a fulgide compound (7) of the following formula.

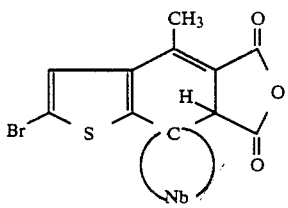

This compound was purified by chromatography on silica gel using benzene/ether as an eluent, and recrystallization from chloroform and hexane gave it as yellow needles (melting point 193°–195° C.) in a yield of 34%. The elemental analysis values of this compound were C 52.93%, H 3.92%, S 8.48%, and Br 20.98% agreed with the calculated values for $C_{17}H_{15}O_3SBr$ (C 53.84%, H 3.96%, S 8.46%, and Br 21.09%).

The proton-NMR spectrum of the resulting compound was measured. The spectrum showed a peak of 1H based on the proton of the thiophene ring near $\delta 7.2$ ppm, a peak of 1H 1-5 shifted near $\delta 4.0$ ppm, a peak of 3H based on the protons of the $>C-CH_3$ bond near $\delta 2.6$ ppm, and a broad peak of 10H based on the protons of the norbornylidene near $\delta 1.2-2.5$ ppm. The $^{13}C$-NMR spectrum ($^{13}C$-NMR) of the resulting compound was also measured. The spectrum showed a peak based on the carbons of the norbornylidene group near $\delta 27-52$ ppm, a peak based on the carbon of the methyl group near $\delta 15.6$ ppm, a peak based on the carbons of the thiophene ring near $\delta 110-160$ ppm, and a peak based on the carbon of the $>C=O$ bond near $\delta 160-170$ ppm.

From the above results, the isolated product was identified as a compound of the structural formula (7).

EXAMPLE 8

In the same way as in Examples 1 to 7, various compounds were synthesized from the starting materials shown in Table 1-A. The yields of the products are shown in Table 1-A.

By the same elemental analysis, proton NMR spectral analysis and $^{13}C$-NMR spectral analysis as in Examples 1 to 7, the resulting compounds were determined to have the structures shown in Table 1-A.

The results of the elemental analysis are shown in Table 1-B.

TABLE 1-A

| No. | Starting materials | Product | Yield (%) |
|---|---|---|---|
| 8 | H₂NCH₂NO₂ | | 21 |
| 9 | H₂NCH₂Cl | | 19 |
| 10 | H₂NCH₂CCH₃ ‖ O | | 16 |

TABLE 1-A-continued

| No. | Starting materials | Product | Yield (%) |
|---|---|---|---|
| 11 | | | 23 |
| 12 | | | 26 |
| 13 | | | 24 |

TABLE 1-A-continued

| No. | Starting materials | Product | Yield (%) |
|---|---|---|---|
| 14 | (structure) + H₂NCH₂COCCH₂CH₂CN with CH₃ and OCH₃ | (product structure with NCH₂COCCH₂CH₂CN group) | 21 |
| 15 | (structure) + H₂NCH₂CH₂CCH₂CH₂CNCH₃ with H and O | (product structure with NCH₂CH₂CH₂CH₂CNCH₃ group) | 19 |
| 16 | (structure) + H₂NCH₂OCH₂CH₂OCH₃ | (product structure with NCH₂OCH₂CH₂OCH₃ group) | 21 |

TABLE 1-A-continued

| No. | Starting materials | Product | Yield (%) |
|---|---|---|---|
| 17 | [structure: anhydride with phenyl, dimethoxyphenyl, and adamantyl-C4H9 substituents] + CH3-C(NH2)(CH3)-CN | [structure: imide with N-C(CH3)2-CN, phenyl, dimethoxyphenyl, and adamantyl-C4H9 substituents] | 18 |
| 18 | [structure: anhydride with C2H5, thiophene-phenyl, and perfluoro-cage substituents] + H2NCH2CCH2CH2CCH2Cl (with two C=O) | [structure: imide with N-CH2CCH2CH2CCH2Cl, C2H5, thiophene-phenyl, and perfluoro-cage substituents] | 16 |

TABLE 1-A-continued

| No. | Starting materials | Product | Yield (%) |
|---|---|---|---|
| 19 | | | 21 |
| 20 | | | 19 |
| 21 | | | 23 |

TABLE 1-A-continued

| No. | Starting materials | Product | Yield (%) |
|---|---|---|---|
| 22 | | | 21 |
| 23 | | | 25 |
| 24 | | | 26 |

TABLE 1-A

| No. | Starting materials | Product | Yield (%) |
|---|---|---|---|
| 25 | H₂NCH₂CN—CH₂CH₂Br with OH | (structure) | 21 |
| 26 | (cyclohexane with CN and H₂N-CH₂) | (structure) | 20 |
| 27 | BrCH₂COCH₃ + (imide NH structure) | (structure) | 25 |

-continued
TABLE 1-A

| No. | Starting materials | Product | Yield (%) |
|---|---|---|---|
| 28 | BrCH₂CN | | 11 |
| 29 | BrCH₂COCH₂CH₂CN | | 35 |
| 30 | BrCHCH₂NO₂ with C₂H₅ | | 40 |

-continued
TABLE 1-A

| No. | Starting materials | Product | Yield (%) |
|---|---|---|---|
| 31 | BrCH₂CNCH₂CH₂Cl ∥ OH | | 36 |
| 32 | CH₃ BrCHCCH₃ ∥ O | | 27 |
| 33 | (2-bromocyclohexanecarbonitrile) | | 37 |

-continued
TABLE 1-A

| No. | Starting materials | Product | Yield (%) |
|-----|-------------------|---------|-----------|
| 34 | | | 36 |
| 35 | | | 29 |
| 36 | | | 31 |

-continued
TABLE 1-A

| No. | Starting materials | Product | Yield (%) |
|---|---|---|---|
| 37 | BrCH₂CF₃ | | 33 |
| 38 | BrCH₂COCH₂CH₂Cl ‖ O | | 30 |
| 39 | H₂NCH₂CH₂COCH₃ ‖ O | | 18 |

TABLE 1-A

| No. | Starting materials | Product | Yield (%) |
|---|---|---|---|
| 40 | | | 21 |
| 41 | | | 23 |

-continued
TABLE 1-A

| No. | Starting materials | Product | Yield (%) |
|---|---|---|---|
| 42 | | | 25 |
| 43 | | | 26 |

-continued
TABLE 1-A

| No. | Starting materials | Product | Yield (%) |
|---|---|---|---|
| 44 | | | 23 |
| 45 | | | 25 |
| 46 | | | 24 |

-continued
TABLE 1-A

| No. | Starting materials | Product | Yield (%) |
|---|---|---|---|
| 47 | | | 22 |
| 48 | | | 21 |
| 49 | | | 27 |

-continued
TABLE 1-A

| No. | Starting materials | Product | Yield (%) |
|---|---|---|---|
| 50 | | | 48 |
| 51 | | | 51 |
| 52 | | | 52 |

-continued
TABLE 1-A

| No. | Starting materials | Product | Yield (%) |
|---|---|---|---|
| 53 | | | 51 |
| 54 | | | 53 |
| 55 | | | 47 |

-continued
TABLE 1-A

| No. | Starting materials | Product | Yield (%) |
|---|---|---|---|
| 56 | | | 41 |
| 57 | | | 53 |
| 58 | | | 50 |

TABLE 1-A

| No. | Starting materials | | Product | Yield (%) |
|---|---|---|---|---|
| 59 | | | | 57 |
| 60 | | | | 56 |
| 61 | | | | 49 |

-continued
TABLE 1-A

| No. | Starting materials | | Product | Yield (%) |
|---|---|---|---|---|
| 62 | [structure] | H₂NCH₂CH₂OCH₂-[2-naphthyl] | [structure] | 25 |
| 63 | [structure] | H₂NCH₂CH₂OCH₂-[1-naphthyl] | [structure] | 24 |
| 64 | [structure] | H₂N—CH(C₂H₅)—CO—CH₂-[1-naphthyl] | [structure] | 21 |

-continued
TABLE 1-A

| No. | Starting materials | Product | Yield (%) |
|---|---|---|---|
| 65 | | | 28 |
| 66 | | | 26 |
| 67 | | | 13 |

-continued
TABLE 1-A

| No. | Starting materials | Product | Yield (%) |
|---|---|---|---|
| 68 | | | 26 |
| 69 | | | 20 |
| 70 | | | 26 |

-continued
TABLE 1-A

| No. | Starting materials | Product | Yield (%) |
|---|---|---|---|
| 71 | | | 17 |
| 72 | | | 21 |
| 73 | | | 51 |

TABLE 1-A

| No. | Starting materials | Product | Yield (%) |
|---|---|---|---|
| 74 | | | 53 |
| 75 | | | 49 |
| 76 | | | 60 |

-continued
TABLE 1-A

| No. | Starting materials | Product | Yield (%) |
|---|---|---|---|
| 77 | | | 58 |
| 78 | | | 51 |
| 79 | | | 54 |

-continued
TABLE 1-A

| No. | Starting materials | Product | Yield (%) |
|---|---|---|---|
| 80 | | | |
| 81 | | | |
| | | | 54 |
| | | | 59 |

-continued
TABLE 1-A
| No. | Starting materials | Product | Yield (%) |
|---|---|---|---|
| 82 | 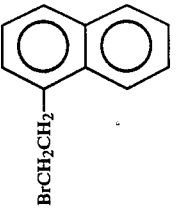 | 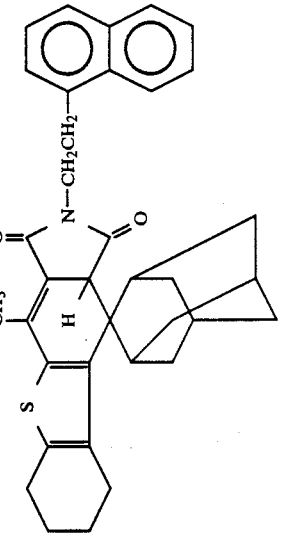 | 52 |
| 83 | 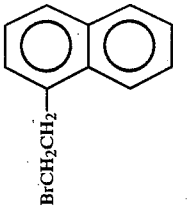 | 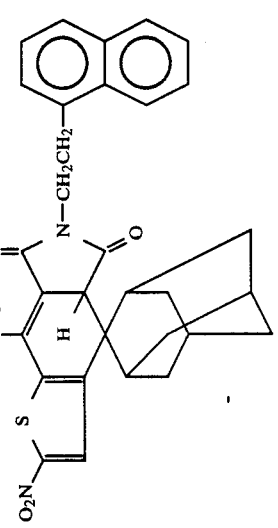 | 57 |
| 84 | 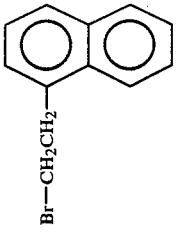 | 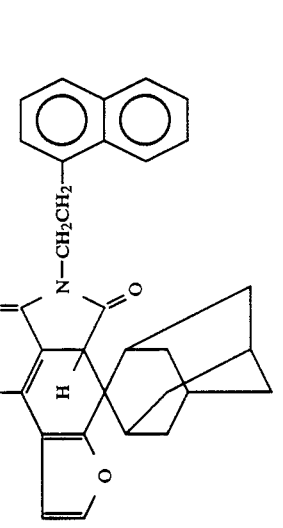 | 51 |

-continued
TABLE 1-A

| No. | Starting materials | Product | Yield (%) |
|---|---|---|---|
| 85 | | | 57 |
| 86 | | | 23 |
| 87 | | | 32 |

TABLE 1-A

| No. | Starting materials | Product | Yield (%) |
|---|---|---|---|
| 88 | | | 30 |
| 89 | " | | 19 |
| 90 | " | | 11 |

| No. | Starting materials | | Product | Yield (%) |
|---|---|---|---|---|
| 91 | 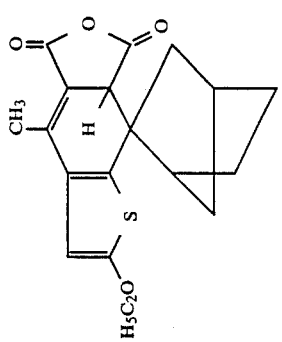 | 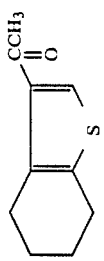 | 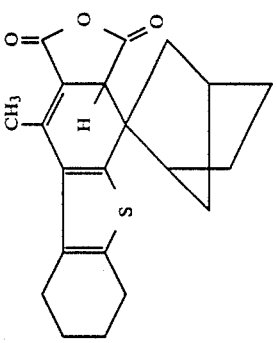 | 12 |
| 92 | 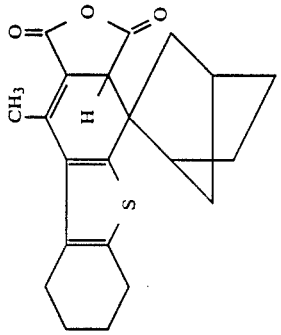 | " | 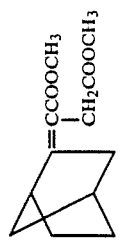 | 26 |
| 93 | 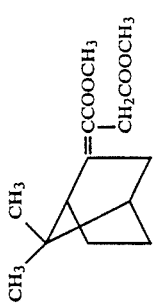 |  |  | 10 |

-continued
TABLE 1-A

| No. | Starting materials | Product | Yield (%) |
|---|---|---|---|
| 94 | | | 9 |
| 95 | | | 24 |
| 96 | | | 23 |

-continued
TABLE 1-A

| No. | Starting materials | Product | Yield (%) |
|---|---|---|---|
| 97 | aniline | (structure) | 23 |
| 98 | 4-methylaniline | (structure) | 32 |
| 99 | C₂H₅—NH₂ | (structure) | 16 |

-continued
TABLE 1-A
| No. | Starting materials | Product | Yield (%) |
|---|---|---|---|
| 100 | NH$_3$ | 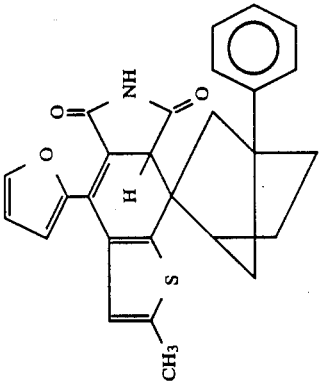 | 19 |

TABLE 1-B

| | Elemental analysis (%) | | | | | | | | | | | |
|---|---|---|---|---|---|---|---|---|---|---|---|---|
| | Calculated | | | | | | Found | | | | | |
| No. | C | H | N | O | S | Others | C | H | N | O | S | Others |
| 8 | 64.08 | 5.83 | 6.80 | 15.52 | 7.77 | — | 64.12 | 5.81 | 6.84 | 15.50 | 7.73 | — |
| 9 | 66.75 | 5.56 | 2.99 | 10.27 | 6.85 | Cl 7.58 | 66.71 | 5.52 | 2.93 | 10.35 | 6.88 | Cl 7.61 |
| 10 | 76.55 | 5.82 | 2.63 | 9.00 | 6.00 | — | 76.51 | 5.80 | 2.67 | 8.98 | 6.04 | — |
| 11 | 60.66 | 5.49 | 9.23 | 17.59 | 7.03 | — | 60.71 | 5.52 | 9.17 | 17.53 | 7.07 | — |
| 12 | 68.85 | 5.54 | 2.77 | 15.83 | — | Cl 7.01 | 68.91 | 5.50 | 2.72 | 15.79 | — | Cl 7.08 |
| 13 | 57.87 | 4.61 | 5.87 | 10.07 | 6.71 | Cl 14.87 | 57.89 | 4.60 | 5.92 | 10.09 | 6.67 | Cl 14.83 |
| 14 | 71.22 | 6.47 | 5.04 | 17.27 | — | — | 71.26 | 6.42 | 5.08 | 17.24 | — | — |
| 15 | 70.88 | 7.54 | 8.55 | 13.03 | — | — | 70.93 | 7.52 | 8.59 | 12.96 | — | — |
| 16 | 67.61 | 5.84 | 2.82 | 16.08 | — | F 7.65 | 67.70 | 5.80 | 2.84 | 16.06 | — | F 7.60 |
| 17 | 76.82 | 7.27 | 4.84 | 11.07 | — | — | 76.80 | 7.31 | 4.78 | 11.11 | — | — |
| 18 | 46.42 | 2.25 | 1.75 | 7.99 | 3.99 | Cl 4.42 F 33.19 | 46.37 | 2.24 | 1.79 | 7.96 | 4.02 | Cl 4.46 F 33.16 |
| 19 | 56.11 | 5.29 | 2.85 | 13.01 | 6.51 | Br 16.24 | 56.19 | 5.24 | 2.86 | 12.86 | 6.56 | Br 16.29 |
| 20 | 65.57 | 6.38 | 7.65 | 20.40 | — | — | 65.64 | 6.42 | 7.60 | 20.34 | — | — |
| 21 | 63.36 | 7.14 | 2.17 | 9.94 | 4.97 | Br 12.41 | 63.43 | 7.09 | 2.19 | 9.87 | 5.02 | Br 12.40 |
| 22 | 72.56 | 6.05 | 6.51 | 7.44 | 7.44 | — | 72.50 | 6.11 | 6.53 | 7.39 | 7.47 | — |
| 23 | 66.98 | 5.95 | 2.60 | 17.86 | — | Cl 6.60 | 67.04 | 5.92 | 2.65 | 17.85 | — | Cl 6.54 |
| 24 | 67.30 | 5.61 | 4.76 | 16.31 | — | Cl 6.02 | 67.39 | 5.70 | 4.69 | 16.22 | — | Cl 6.00 |
| 25 | 50.06 | 4.55 | 5.31 | 12.14 | 6.07 | Cl 6.72 Br 15.15 | 50.12 | 4.49 | 5.37 | 12.04 | 6.12 | Cl 6.77 Br 15.09 |
| 26 | 75.92 | 7.91 | 4.92 | 5.62 | 5.62 | — | 75.86 | 7.94 | 4.96 | 5.65 | 5.59 | — |
| 27 | 67.15 | 6.08 | 3.41 | 15.57 | 7.79 | — | 67.21 | 6.11 | 3.36 | 15.60 | 7.72 | — |
| 28 | 72.93 | 6.08 | 7.73 | 13.26 | — | — | 72.87 | 6.14 | 7.67 | 13.32 | — | — |
| 29 | 71.40 | 6.65 | 7.35 | 8.40 | — | Cl 6.20 | 71.49 | 6.60 | 7.32 | 8.35 | — | Cl 6.24 |
| 30 | 66.67 | 7.07 | 4.71 | 21.55 | — | — | 66.74 | 7.02 | 4.64 | 21.60 | — | — |
| 31 | 67.50 | 6.12 | 4.63 | 10.60 | 5.29 | Cl 5.86 | 67.59 | 6.17 | 4.56 | 10.63 | 5.22 | Cl 5.83 |
| 32 | 70.07 | 7.06 | 3.41 | 19.46 | — | — | 70.12 | 7.12 | 3.34 | 19.44 | — | — |
| 33 | 67.24 | 6.03 | 6.03 | 6.90 | 13.79 | — | 67.19 | 6.06 | 6.09 | 6.82 | 13.84 | — |
| 34 | 61.16 | 5.95 | 1.98 | 11.33 | 4.53 | Cl 15.06 | 61.24 | 5.89 | 1.94 | 11.34 | 4.57 | Cl 15.02 |
| 35 | 68.00 | 6.03 | 2.56 | 17.55 | 5.85 | — | 68.02 | 6.09 | 2.52 | 17.48 | 5.89 | — |
| 36 | 65.93 | 6.37 | 3.08 | 17.58 | 7.03 | — | 65.99 | 6.41 | 3.02 | 17.49 | 7.09 | — |
| 37 | 65.19 | 5.43 | 3.46 | 11.85 | 14.07 | — | 65.22 | 5.49 | 3.41 | 11.86 | 14.02 | — |
| 38 | 63.98 | 5.50 | 2.41 | 11.01 | 11.01 | Cl 6.10 | 64.04 | 5.46 | 2.44 | 10.96 | 11.08 | Cl 6.02 |
| 39 | 65.79 | 5.32 | 2.33 | 13.29 | — | Br 13.27 | 65.81 | 5.34 | 2.31 | 13.25 | — | Br 13.29 |
| 40 | 77.49 | 6.11 | 2.44 | 13.96 | — | — | 77.61 | 6.02 | 2.37 | 14.00 | — | — |
| 41 | 65.72 | 4.61 | 2.02 | 11.53 | 4.61 | Br 11.51 | 65.78 | 4.53 | 2.05 | 11.43 | 4.64 | Br 11.57 |
| 42 | 78.53 | 5.52 | 2.86 | 6.54 | 6.54 | — | 78.50 | 5.57 | 2.88 | 6.55 | 6.50 | — |
| 43 | 73.51 | 5.96 | 4.64 | 15.89 | — | — | 73.56 | 5.91 | 4.60 | 15.93 | — | — |
| 44 | 73.21 | 5.95 | 4.17 | 11.90 | 4.76 | — | 73.17 | 5.91 | 4.21 | 11.92 | 4.79 | — |
| 45 | 71.10 | 5.93 | 4.48 | 12.81 | — | Cl 5.68 | 71.04 | 5.97 | 4.39 | 12.88 | — | Cl 5.72 |
| 46 | 65.89 | 5.94 | 2.08 | 14.25 | — | Br 11.86 | 65.81 | 5.97 | 2.09 | 14.24 | — | Br 11.89 |
| 47 | 69.32 | 6.11 | 2.31 | 5.28 | 5.28 | Cl 11.70 | 69.27 | 6.16 | 2.35 | 5.24 | 5.32 | Cl 11.66 |
| 48 | 80.25 | 7.32 | 2.23 | 5.10 | 5.10 | — | 80.20 | 7.38 | 2.17 | 5.09 | 5.16 | — |
| 49 | 62.51 | 4.88 | 2.28 | 13.02 | — | Cl 17.31 | 62.57 | 4.83 | 2.31 | 12.95 | — | Cl 17.34 |
| 50 | 69.19 | 5.95 | 7.57 | 11.53 | 5.77 | — | 69.24 | 5.91 | 7.64 | 11.48 | 5.73 | — |
| 51 | 80.52 | 6.71 | 2.29 | 5.24 | 5.24 | — | 80.59 | 6.67 | 2.24 | 5.24 | 5.26 | — |
| 52 | 64.59 | 5.21 | 2.43 | 8.33 | 5.56 | Br 13.87 | 64.62 | 5.18 | 2.39 | 8.31 | 5.59 | Br 13.91 |
| 53 | 67.44 | 5.19 | 2.02 | 9.22 | 4.61 | Br 11.51 | 67.51 | 5.14 | 2.09 | 9.05 | 4.65 | Br 11.56 |
| 54 | 75.62 | 6.14 | 2.32 | 10.61 | 5.31 | — | 75.69 | 6.11 | 2.26 | 10.66 | 5.28 | — |
| 55 | 64.66 | 4.88 | 2.36 | 16.16 | — | Cl 11.94 | 64.72 | 4.83 | 2.39 | 16.15 | — | Cl 11.91 |
| 56 | 77.76 | 5.78 | 2.45 | 14.01 | — | — | 77.81 | 5.72 | 2.42 | 14.05 | — | — |
| 57 | 75.00 | 6.76 | 4.73 | 13.51 | — | — | 74.91 | 6.82 | 4.70 | 13.57 | — | — |
| 58 | 65.15 | 5.08 | 7.36 | 16.81 | 5.60 | — | 65.22 | 5.04 | 7.34 | 16.76 | 5.64 | — |
| 59 | 78.73 | 5.77 | 2.78 | 12.72 | — | — | 78.79 | 5.71 | 2.81 | 12.69 | — | — |
| 60 | 76.43 | 6.37 | 4.46 | 12.74 | — | — | 76.37 | 6.29 | 4.52 | 12.82 | — | — |
| 61 | 60.89 | 4.58 | 4.58 | 13.10 | 5.24 | Cl 11.61 | 60.82 | 4.54 | 4.62 | 13.09 | 5.29 | Cl 11.64 |
| 62 | 75.98 | 6.52 | 2.61 | 8.94 | 5.96 | — | 75.91 | 6.58 | 2.64 | 8.88 | 5.99 | — |
| 63 | 77.68 | 6.30 | 2.39 | 8.18 | 5.45 | — | 77.74 | 6.26 | 2.42 | 8.10 | 5.48 | — |
| 64 | 76.76 | 6.08 | 2.18 | 9.98 | 4.99 | — | 76.72 | 6.10 | 2.14 | 10.03 | 5.01 | — |
| 65 | 67.09 | 5.43 | 4.47 | 17.89 | 5.11 | — | 67.11 | 5.40 | 4.51 | 17.90 | 5.08 | — |
| 66 | 72.73 | 5.26 | 6.70 | 15.31 | — | — | 72.97 | 5.17 | 6.72 | 15.32 | — | — |
| 67 | 76.76 | 6.61 | 2.99 | 6.82 | 6.82 | — | 76.81 | 6.64 | 2.94 | 6.84 | 6.77 | — |
| 68 | 78.30 | 6.36 | 2.28 | 13.05 | — | — | 78.21 | 6.41 | 2.30 | 13.08 | — | — |
| 69 | 79.00 | 6.58 | 4.39 | 10.03 | — | — | 79.07 | 6.51 | 4.41 | 10.01 | — | — |
| 70 | 80.13 | 6.84 | 2.34 | 10.68 | — | — | 80.17 | 6.81 | 2.30 | 10.72 | — | — |
| 71 | 80.67 | 6.22 | 2.35 | 10.76 | — | — | 80.62 | 6.27 | 2.32 | 10.79 | — | — |
| 72 | 79.40 | 5.86 | 2.65 | 6.05 | 6.05 | — | 79.47 | 5.81 | 2.67 | 6.03 | 6.02 | — |
| 73 | 74.18 | 6.18 | 5.09 | 8.73 | 5.82 | — | 74.22 | 6.11 | 5.12 | 8.64 | 5.86 | — |
| 74 | 74.34 | 6.19 | 2.48 | 11.33 | 5.66 | — | 74.38 | 6.22 | 2.42 | 11.38 | 5.60 | — |
| 75 | 72.68 | 6.06 | 1.88 | 19.38 | — | — | 72.61 | 6.12 | 1.84 | 19.43 | — | — |
| 76 | 76.90 | 6.71 | 2.09 | 9.54 | 4.77 | — | 76.97 | 6.64 | 2.12 | 9.54 | 4.73 | — |
| 77 | 68.81 | 5.87 | 1.87 | 8.53 | 4.27 | Br 10.65 | 68.88 | 5.82 | 1.89 | 8.48 | 4.24 | Br 10.69 |
| 78 | 70.35 | 5.86 | 2.35 | 16.08 | 5.36 | — | 70.39 | 5.88 | 2.31 | 16.10 | 5.32 | — |
| 79 | 66.06 | 6.29 | 3.67 | 14.68 | — | Cl 9.29 | 66.12 | 6.24 | 3.62 | 14.79 | — | Cl 9.23 |
| 80 | 68.24 | 5.35 | 2.34 | 5.35 | 5.35 | Br 13.36 | 68.31 | 5.32 | 2.30 | 5.38 | 5.37 | Br 13.32 |
| 81 | 76.52 | 5.51 | 4.06 | 13.91 | — | — | 76.59 | 5.47 | 4.02 | 13.92 | — | — |
| 82 | 78.98 | 6.76 | 2.56 | 5.85 | 5.85 | — | 78.92 | 6.81 | 2.52 | 5.87 | 5.88 | — |
| 83 | 71.38 | 5.58 | 5.20 | 11.90 | 5.95 | — | 71.42 | 5.64 | 5.14 | 11.91 | 5.89 | — |

TABLE 1-B-continued

| | Elemental analysis (%) | | | | | | | | | | | |
|---|---|---|---|---|---|---|---|---|---|---|---|---|
| | Calculated | | | | | | Found | | | | | |
| No. | C | H | N | O | S | Others | C | H | N | O | S | Others |
| 84 | 80.50 | 6.50 | 2.94 | 10.06 | — | — | 80.49 | 6.42 | 2.97 | 10.12 | — | — |
| 85 | 72.50 | 5.20 | 2.35 | 8.06 | — | Cl 11.90 | 72.47 | 5.14 | 2.39 | 8.06 | — | Cl 11.94 |
| 86 | 72.00 | 5.14 | — | 13.71 | 9.14 | — | 72.44 | 5.01 | — | 13.53 | 9.02 | — |
| 87 | 53.84 | 3.96 | — | 12.67 | 8.45 | Br 21.09 | 53.69 | 3.99 | — | 12.64 | 8.52 | Br 21.16 |
| 88 | 68.75 | 6.25 | — | 25.00 | — | — | 68.66 | 6.29 | — | 25.05 | — | — |
| 89 | 78.79 | 5.05 | — | 16.16 | — | — | 78.69 | 5.12 | — | 16.19 | — | — |
| 90 | 77.21 | 6.17 | 3.75 | 12.87 | — | — | 77.29 | 6.12 | 3.70 | 12.89 | — | — |
| 91 | 71.19 | 6.21 | — | 13.56 | 9.04 | — | 71.27 | 6.16 | — | 13.56 | 9.01 | — |
| 92 | 66.28 | 5.81 | — | 18.60 | 9.30 | — | 66.35 | 5.74 | — | 18.65 | 9.26 | — |
| 93 | 64.25 | 4.93 | — | 13.71 | — | Br 17.11 | 64.34 | 4.87 | — | 13.75 | — | Br 17.04 |
| 94 | 77.12 | 6.94 | 3.60 | 12.34 | — | — | 77.02 | 6.98 | 3.69 | 12.31 | — | — |
| 95 | 70.79 | 6.74 | — | 13.48 | 8.99 | — | 70.70 | 6.72 | — | 13.51 | 9.07 | — |
| 96 | 66.82 | 5.12 | 3.12 | 17.82 | 7.13 | — | 66.77 | 5.16 | 3.14 | 17.25 | 7.18 | — |
| 97 | 60.81 | 4.41 | 3.08 | 7.05 | 7.05 | Br 17.60 | 60.89 | 4.37 | 3.02 | 6.89 | 7.08 | Br 17.66 |
| 98 | 76.54 | 5.69 | 3.19 | 7.29 | 7.29 | — | 76.61 | 5.62 | 3.21 | 7.32 | 7.24 | — |
| 99 | 70.07 | 7.06 | 3.41 | 19.46 | — | — | 70.01 | 7.09 | 3.46 | 19.44 | — | — |
| 100 | 76.24 | 5.41 | 3.29 | 7.53 | 7.53 | — | 76.32 | 5.33 | 3.24 | 7.55 | 7.56 | — |

EXAMPLE 9

In each run, 0.5 part by weight of each the compounds represented by structural formulae (1) to (100) produced in Examples 1 to 8, 10 parts by weight of poly(methyl methacrylate) and 100 parts of benzene were dispersed, and the resulting mixture was cast into a film on a slide glass (11.2×3.7 cm). The thickness of the cast film was adjusted to 0.1 mm. Xenon light was irradiated onto the resulting photochromic film by using a xenon long-life fadeometer (FAL-25AX-HC; output 2.5 KW; light source xenon long-life arc lamp) made by Suga Testing Instrument Co., Ltd. The initial coloration density (absorbance), maximum absorption wavelength ($\sigma_{max}$) and fatigue life ($T_{\frac{1}{2}}$) in accordance with JIS L 0843 and JIS B7754 of the photochromic film were measured.

$T_{\frac{1}{2}}$ is defined as the time required for the color density to decrease to half of its initial value when the film is exposed to the fadeometer.

The results of measurements are shown in Table 2. For comparison, the following compounds (X) and (Y) were also tested in the same way as above, and the fatigue life of the resulting photochromic films were measured.

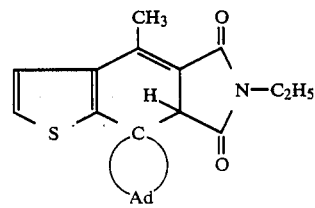 (X)

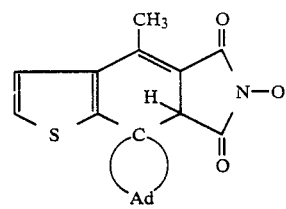 (Y)

TABLE 2

| No. | Fulgimide or fulgide compound No. | Initial color density (%) | $T_{\frac{1}{2}}$ (hours) | $\lambda_{max}$ (nm) |
|---|---|---|---|---|
| 1 | (1) | 0.62 | 38 | 535 |
| 2 | (2) | 0.83 | 46 | 553 |
| 3 | (3) | 0.42 | 13 | 535 |
| 4 | (4) | 0.39 | 21 | 532 |
| 5 | (5) | 0.51 | 24 | 520 |
| 6 | (6) | 0.49 | 16 | 538 |
| 7 | (7) | 0.38 | 15 | 520 |
| 8 | (8) | 0.72 | 30 | 556 |
| 9 | (9) | 0.59 | 30 | 542 |
| 10 | (10) | 0.58 | 40 | 601 |
| 11 | (11) | 0.61 | 39 | 525 |
| 12 | (12) | 0.79 | 31 | 560 |
| 13 | (13) | 0.72 | 41 | 526 |
| 14 | (14) | 0.82 | 42 | 490 |
| 15 | (15) | 0.62 | 38 | 595 |
| 16 | (16) | 0.84 | 31 | 492 |
| 17 | (17) | 0.49 | 48 | 550 |
| 18 | (18) | 0.52 | 41 | 519 |
| 19 | (19) | 0.47 | 43 | 520 |
| 20 | (20) | 0.39 | 40 | 576 |
| 21 | (21) | 0.52 | 36 | 576 |
| 22 | (22) | 0.41 | 49 | 515 |
| 23 | (23) | 0.77 | 40 | 526 |
| 24 | (24) | 0.41 | 29 | 583 |
| 25 | (25) | 0.38 | 33 | 510 |
| 26 | (26) | 0.47 | 44 | 560 |
| 27 | (27) | 0.60 | 38 | 538 |
| 28 | (28) | 0.90 | 48 | 535 |
| 29 | (29) | 0.71 | 44 | 576 |
| 30 | (30) | 0.50 | 36 | 570 |
| 31 | (31) | 0.80 | 37 | 580 |
| 32 | (32) | 0.49 | 38 | 550 |
| 33 | (33) | 0.48 | 43 | 590 |
| 34 | (34) | 0.59 | 36 | 590 |
| 35 | (35) | 0.79 | 41 | 580 |
| 36 | (36) | 0.72 | 42 | 575 |
| 37 | (37) | 0.91 | 37 | 535 |
| 38 | (38) | 0.70 | 34 | 575 |
| 39 | (39) | 0.38 | 34 | 492 |
| 40 | (40) | 0.37 | 24 | 489 |
| 41 | (41) | 0.30 | 21 | 520 |
| 42 | (42) | 0.32 | 10 | 513 |
| 43 | (43) | 0.34 | 22 | 540 |
| 44 | (44) | 0.33 | 23 | 586 |
| 45 | (45) | 0.27 | 24 | 582 |
| 46 | (46) | 0.41 | 22 | 495 |
| 47 | (47) | 0.52 | 13 | 529 |
| 48 | (48) | 0.67 | 10 | 585 |
| 49 | (49) | 0.49 | 20 | 503 |
| 50 | (50) | 0.32 | 14 | 535 |
| 51 | (51) | 0.33 | 15 | 592 |
| 52 | (52) | 0.31 | 20 | 535 |
| 53 | (53) | 0.27 | 17 | 507 |

TABLE 2-continued

| No. | Fulgimide or fulgide compound No. | Initial color density (%) | $T_{\frac{1}{2}}$ (hours) | $\lambda_{max}$ (nm) |
|---|---|---|---|---|
| 54 | (54) | 0.69 | 22 | 509 |
| 55 | (55) | 0.70 | 22 | 499 |
| 56 | (56) | 0.41 | 23 | 546 |
| 57 | (57) | 0.51 | 24 | 592 |
| 58 | (58) | 0.32 | 22 | 556 |
| 59 | (59) | 0.47 | 20 | 486 |
| 60 | (60) | 0.49 | 21 | 562 |
| 61 | (61) | 0.50 | 21 | 512 |
| 62 | (62) | 0.60 | 21 | 529 |
| 63 | (63) | 0.65 | 22 | 584 |
| 64 | (64) | 0.70 | 21 | 596 |
| 65 | (65) | 0.70 | 17 | 547 |
| 66 | (66) | 0.80 | 19 | 556 |
| 67 | (67) | 0.42 | 12 | 515 |
| 68 | (68) | 0.85 | 21 | 487 |
| 69 | (69) | 0.60 | 21 | 576 |
| 70 | (70) | 0.90 | 22 | 490 |
| 71 | (71) | 0.60 | 11 | 579 |
| 72 | (72) | 0.52 | 12 | 498 |
| 73 | (73) | 0.42 | 24 | 515 |
| 74 | (74) | 0.53 | 23 | 515 |
| 75 | (75) | 0.77 | 21 | 480 |
| 76 | (76) | 0.82 | 14 | 488 |
| 77 | (77) | 0.82 | 19 | 597 |
| 78 | (78) | 0.72 | 20 | 529 |
| 79 | (79) | 0.87 | 13 | 478 |
| 80 | (80) | 0.85 | 12 | 537 |
| 81 | (81) | 0.51 | 20 | 581 |
| 82 | (82) | 0.47 | 13 | 508 |
| 83 | (83) | 0.44 | 13 | 492 |
| 84 | (84) | 0.81 | 12 | 470 |
| 85 | (85) | 0.62 | 12 | 470 |
| 86 | (86) | 0.41 | 10 | 550 |
| 87 | (87) | 0.29 | 12 | 510 |
| 88 | (88) | 0.28 | 8 | 550 |
| 89 | (89) | 0.44 | 13 | 530 |
| 90 | (90) | 0.32 | 9 | 526 |
| 91 | (91) | 0.33 | 11 | 555 |
| 92 | (92) | 0.31 | 12 | 534 |
| 93 | (93) | 0.51 | 12 | 518 |
| 94 | (94) | 0.49 | 12 | 546 |
| 95 | (95) | 0.53 | 11 | 540 |
| 96 | (96) | 0.64 | 9 | 521 |
| 97 | (97) | 0.31 | 8 | 506 |
| 98 | (98) | 0 25 | 11 | 513 |
| 99 | (99) | 0.24 | 8 | 510 |
| 100 | (100) | 0.31 | 8 | 508 |
| Comparison |  |  |  |  |
| 1 | (X) | 0.70 | 3 | 530 |
| 2 | (Y) | 0.60 | 3.5 | 535 |

The fading speeds of the cast films prepared as above were measured by the following procedure.

The cast film was exposed to a mercury lamp (SHL-100 made by Toshiba Co., Ltd.) at 20°±1° C. for 60 seconds from a distance of 10 cm. Then, the irradiation was stopped, and the fading speed was determined from changes in the absorbance of the cast film measured by a spectrophotometer (220A made by Hitachi Limited). The fading speed is expressed by the time which is required to the absorbance of the cast film to a value half of (the absorbance of the cast film at a maximum absorption wavelength immediately after 60 second irradiation)—(the absorbance of the non-irradiated cast film at the maximum wavelength) after light irradiation for 60 seconds. The results are shown in Table 3.

TABLE 3

| No. | No. of the fulgimide compound | Fading speed (seconds) |
|---|---|---|
| 1 | (1) | 39 |
| 2 | (2) | 26 |
| 3 | (3) | 71 |
| 4 | (4) | 52 |
| 5 | (5) | 58 |
| 6 | (6) | 76 |
| 7 | (7) | 21 |
| Comparison | (Y) | 120 |

EXAMPLE 10

0.1 g of each of the fulgimide or fulgide compounds produced in Examples 1 to 8 was dissolved in 100 cc of silicone oil. The solution was impregnated in the surface of a lens composed of poly(allyl diglycol carbonate) at 200° C. for 1 hour. The concentration of the solution was adjusted to $1.0 \times 10^{-4}$ mole/g. The durability of the film was measured as in Example 9. The results are shown in Table 4.

TABLE 4

| No. | Fulgimide or fulgide compound No. | $T_{\frac{1}{2}}$ (hours) | $\lambda_{max}$ (nm) | Initial color density (%) |
|---|---|---|---|---|
| 1 | (1) | 40 | 540 | 0.50 |
| 2 | (2) | 50 | 562 | 0.64 |
| 3 | (5) | 31 | 520 | 0.40 |
| 4 | (8) | 32 | 562 | 0.56 |
| 5 | (10) | 43 | 610 | 0.47 |
| 6 | (14) | 42 | 500 | 0.63 |
| 7 | (24) | 33 | 590 | 0.32 |
| 8 | (28) | 49 | 540 | 0.72 |
| 9 | (29) | 45 | 583 | 0.56 |
| 10 | (41) | 25 | 524 | 0.24 |
| 11 | (53) | 21 | 515 | 0.21 |
| 12 | (55) | 24 | 505 | 0.56 |
| 13 | (61) | 24 | 521 | 0.40 |
| 14 | (62) | 25 | 530 | 0.48 |
| 15 | (64) | 24 | 598 | 0.56 |
| 16 | (68) | 23 | 495 | 0.68 |
| 17 | (78) | 21 | 534 | 0.57 |
| 18 | (82) | 14 | 515 | 0.38 |
| 19 | (83) | 14 | 499 | 0.33 |
| 20 | (85) | 14 | 478 | 0.56 |

EXAMPLE 11

One hundred parts of benzene, 10 parts of poly(-methyl methacrylate), 0.2 part of the fulgimide compound obtained in Example 1 and 0.2 part of each of the compounds shown in Table 5 as an ultraviolet stabilizer were mixed to form a solution. The solution was cast on a slide glass (11.2×3.7 cm) to form a cast film having a thickness of 0.1 mm.

The fatigue life of photochromic film was measured as in Example 9 by a xenon long-life fadeometer (FAL-25AX-HC made by Suga Testing Instrument Co., Ltd.). The results are shown in Table 5.

TABLE 5

| No. | Ultraviolet stabilizer | $T_{\frac{1}{2}}$ (hours) |
|---|---|---|
| 1 | Cyasorb UV1084 | 152 |
| 2 | Irgastab 2002 | 147 |
| 3 | Rylex NBC | 158 |
| 4 | UV Chek AM101 | 144 |
| 5 | UV Chek AM105 | 133 |
| 6 | UV Chek AM126 | 168 |
| 7 | Tinuvin 765 | 159 |

TABLE 5-continued

| No. | Ultraviolet stabilizer | T₁ (hours) |
|---|---|---|
| 8 | Chimassorb 944 | 138 |
| 9 | Cyasorb 3346 | 165 |
| 10 | Tinuvin 622 | 160 |
| 11 | Spinuvex A-36 | 148 |
| 12 | Tinuvin 144 | 152 |

EXAMPLE 12

Example 11 was repeated except that the fulgimide compound obtained in Example 2 was used instead of fulgimide compound used in Example 11. The results are shown in Table 6.

TABLE 6

| No. | Ultraviolet stabilizer | T₁ (hours) |
|---|---|---|
| 1 | Cyasorb UV1084 | 182 |
| 2 | Irgastab 2002 | 176 |
| 3 | Rylex NBC | 190 |
| 4 | UV Chek AM101 | 173 |
| 5 | UV Chek AM105 | 160 |
| 6 | UV Chek AM126 | 196 |
| 7 | Tinuvin 765 | 191 |
| 8 | Chimassorb 944 | 166 |
| 9 | Cyasorb 3346 | 198 |
| 10 | Tinuvin 622 | 192 |
| 11 | Spinuvex A-36 | 178 |
| 12 | Tinuvin 144 | 182 |

EXAMPLE 13

Example 11 was repeated except that each of the ultraviolet stabilizers shown in Table 7 was used. The results are summarized in Table 7.

TABLE 7

| Run | Type | Amount added | Proportion per 100 parts by weight of the fulgimide compound (parts by weight) | T₁ (hours) |
|---|---|---|---|---|
| 1 | Cyasorb UV1084 | 0.002 | 1 | 110 |
| 2 | Cyasorb UV1084 | 0.1 | 50 | 140 |
| 3 | Cyasorb UV1084 | 20 | 10000 | 180 |
| 4 | Cyasorb UV1084 | 0.8 | 400 | 160 |
| 5 | Tinuvin 765 | 0.002 | 1 | 106 |
| 6 | Tinuvin 765 | 0.1 | 50 | 152 |
| 7 | Tinuvin 765 | 20 | 10000 | 182 |
| 8 | Tinuvin 765 | 0.8 | 400 | 166 |

EXAMPLE 14

Example 11 was repeated except that the fulgimide or fulgide compounds shown in Table 8 were used instead of the fulgimide compounds used in Example 11, and Cyasorb UV1084 was used as the ultraviolet stabilizer. The results are shown in Table 8.

TABLE 8

| No. | Fulgimide or fulgide compound | T₁ (hours) |
|---|---|---|
| 1 | (2) | 182 |
| 2 | (3) | 77 |
| 3 | (4) | 81 |
| 4 | (6) | 65 |
| 5 | (12) | 160 |
| 6 | (17) | 188 |
| 7 | (36) | 186 |
| 8 | (41) | 77 |
| 9 | (50) | 52 |
| 10 | (53) | 52 |
| 11 | (60) | 78 |
| 12 | (62) | 80 |
| 13 | (67) | 80 |
| 14 | (72) | 51 |
| 15 | (81) | 66 |

We claim:

1. A composition comprising a high-molecular-weight polymer and a compound represented by general formula (I)

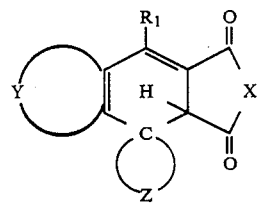

[I]

wherein

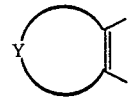

represents a divalent aromatic hydrocarbon group or a divalent unsaturated heterocyclic group each of which may have a substituent, $R_1$ represents a monovalent hydrocarbon group or a monovalent heterocyclic group each of which may have a substituent,

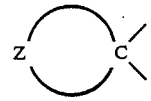

represents a norbornylidene group or an adamantylidene group each of which may have a substituent, and X represents an oxygen atom, the group $>N-R_2$, the group $>N-A_1-B_1-(A_2)_m(B_2)_n-R_3$, the group $>N-A_3-A_4$, or the group $>N-A_3-R_4$, provided that when

is an adamantylidene group, X is selected from the above groups excepting the oxygen atom and the group $>N-R_2$, in which $R_2$ represents a hydrogen atom, an alkyl group having 1 to 20 carbon atoms, or an aryl group having 6 to 10 carbon atoms, $A_1$ and $A_2$ are identical or different and each represents an alkylene group having 1 to 10 carbon atoms, an alkylidene group having 2 to 10 carbon atoms, a cycloalkylene group having 3 to 10 carbon atoms or an alkylcycloalkanediyl group having 6 to 10 carbon atoms, $B_1$ and $B_2$ are identical or different, and each represents

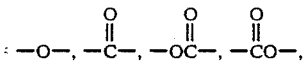

m and n, independently from each other, represent 0 or 1, provided that when m is 0, n is also 0, $R_3$ represents an alkyl group having 1 to 10 carbon atoms, a naphthyl group or a naphthylalkyl group having 1 to 4 carbon atoms in the alkyl moiety, the alkyl group having 1 to 10 carbon atoms being optionally substituted by 1 to 3 atoms or groups selected from the class consisting of halogen atoms, cyano groups and nitro groups, and the naphthyl or naphthylalkyl group being optionally substituted by 1 to 3 atoms or groups selected from the class consisting of halogen atoms, cyano groups, nitro groups, alkylamino groups having 1 to 3 carbon atoms, alkyl groups having 1 to 3 carbon atoms and alkoxy groups having 1 to 3 carbon atoms, $A_3$ represents an alkylene group having 1 to 10 carbon atoms, an alkylidene group having 2 to 10 carbon atoms, a cycloalkylene group having 3 to 10 carbon atoms, or an alkylcycloalkanediyl group having 6 to 10 carbon atoms, $A_4$ represents a naphthyl group which may be substituted by 1 to 3 atoms or groups selected from the class consisting of halogen atoms, cyano groups, nitro groups, alkylamino groups having 1 to 3 carbon atoms, alkyl groups having 1 to 3 carbon atoms and alkoxy groups having 1 to 3 carbon atoms, and $R_4$ represents a halogen atom, a cyano group or a nitro group.

2. The composition of claim 1 which further comprises an ultraviolet stabilizer.

3. The composition of claim 2 in which the ultraviolet stabilizer is a light extinguisher for oxygen in the singlet state or a hindered amine light stabilizer.

4. A photochromic lens composed of any one of the compositions of any one of claims 1 to 3.

* * * * *

UNITED STATES PATENT AND TRADEMARK OFFICE
CERTIFICATE OF CORRECTION

PATENT NO.   :   4,960,678

DATED        :   October 2, 1990

INVENTOR(S)  :   Tanaka et al.

It is certified that error appears in the above-identified patent and that said Letters Patent is hereby corrected as shown below:

On the title page of the patent, Item [30], line 3, change the priority number from "62-80250" to -- 63-80250 --.

Signed and Sealed this

Twentieth Day of October, 1992

*Attest:*

DOUGLAS B. COMER

*Attesting Officer*     *Acting Commissioner of Patents and Trademarks*